(12) United States Patent
Pallin et al.

(10) Patent No.: US 9,440,943 B2
(45) Date of Patent: Sep. 13, 2016

(54) TRICYCLIC SULFONE COMPOUNDS AND METHODS OF MAKING AND USING SAME

(71) Applicant: Zafgen, Inc., Cambridge, MA (US)

(72) Inventors: Thomas D. Pallin, Harlow (GB); Hazel J. Dyke, Harlow (GB); Susan M. Cramp, Harlow (GB); Robert Zahler, Pennington, NJ (US)

(73) Assignee: Zafgen, Inc., Boston, MA (US)

( * ) Notice: Subject to any disclaimer, the term of this patent is extended or adjusted under 35 U.S.C. 154(b) by 0 days.

(21) Appl. No.: 14/372,877

(22) PCT Filed: Jan. 17, 2013

(86) PCT No.: PCT/US2013/021914
§ 371 (c)(1),
(2) Date: Jul. 17, 2014

(87) PCT Pub. No.: WO2013/109735
PCT Pub. Date: Jul. 25, 2013

(65) Prior Publication Data
US 2015/0119456 A1    Apr. 30, 2015

Related U.S. Application Data

(60) Provisional application No. 61/587,825, filed on Jan. 18, 2012.

(51) Int. Cl.
*C07D 311/94* (2006.01)
(52) U.S. Cl.
CPC .................................. *C07D 311/94* (2013.01)
(58) Field of Classification Search
CPC .................................................... C07D 311/94
See application file for complete search history.

(56) References Cited

U.S. PATENT DOCUMENTS

| | | | |
|---|---|---|---|
| 5,164,410 A | 11/1992 | Kishimoto et al. |
| 5,166,172 A | 11/1992 | Kishimoto et al. |
| 5,180,735 A | 1/1993 | Kishimoto et al. |
| 5,180,738 A | 1/1993 | Kishimoto et al. |
| 5,196,406 A | 3/1993 | Kamei et al. |
| 5,204,345 A | 4/1993 | Kishimoto et al. |
| 5,238,950 A | 8/1993 | Clader et al. |
| 5,288,722 A | 2/1994 | Kishimoto et al. |
| 5,290,807 A | 3/1994 | Folkman et al. |
| 5,422,363 A | 6/1995 | Yanai et al. |
| 5,536,623 A | 7/1996 | Ohmachi et al. |
| 5,698,586 A | 12/1997 | Kishimoto et al. |
| 5,767,293 A | 6/1998 | Oku et al. |
| 5,846,562 A | 12/1998 | Yanai et al. |
| 5,900,431 A | 5/1999 | Molina et al. |
| 6,017,949 A | 1/2000 | D'Amato et al. |
| 6,017,954 A | 1/2000 | Folkman et al. |
| 6,040,337 A | 3/2000 | Hong, II et al. |
| 6,063,812 A | 5/2000 | Hong et al. |
| 6,180,626 B1 | 1/2001 | Shimomura et al. |
| 6,207,704 B1 | 3/2001 | Liu et al. |
| 6,242,494 B1 | 6/2001 | Craig et al. |
| 6,268,387 B1 | 7/2001 | Connor et al. |
| 6,306,819 B1 | 10/2001 | Rupnick et al. |
| 6,323,228 B1 | 11/2001 | BaMaung et al. |
| 6,383,471 B1 | 5/2002 | Chen et al. |
| 6,548,477 B1 | 4/2003 | Olson et al. |
| 6,566,541 B2 | 5/2003 | Liu et al. |
| 6,664,244 B1 | 12/2003 | Furuse et al. |
| 6,803,382 B2 | 10/2004 | Eustache et al. |
| 6,887,863 B2 | 5/2005 | Craig et al. |
| 6,989,392 B2 | 1/2006 | Collins et al. |
| 7,005,440 B1 | 2/2006 | Jayyosi et al. |
| 7,030,262 B2 | 4/2006 | BaMaung et al. |
| 7,084,108 B2 | 8/2006 | Olson et al. |
| 7,115,632 B1 | 10/2006 | Bedell et al. |
| 7,268,111 B2 | 9/2007 | Olson et al. |
| 7,282,588 B2 | 10/2007 | Dhanak et al. |
| 7,288,651 B2 | 10/2007 | Deng et al. |
| 7,297,816 B2 | 11/2007 | Allison et al. |
| 7,396,833 B2 | 7/2008 | Xie et al. |
| 7,491,718 B2 | 2/2009 | Comess et al. |
| 7,718,695 B2 | 5/2010 | Kim et al. |
| 8,119,663 B2 | 2/2012 | Heimbach et al. |
| 9,221,787 B2 | 12/2015 | Zahler et al. |
| 9,242,997 B2 | 1/2016 | Cramp et al. |
| 9,266,896 B2 | 2/2016 | Clark et al. |
| 9,290,472 B2 | 3/2016 | Cramp et al. |
| 2002/0002152 A1 | 1/2002 | Craig et al. |
| 2004/0019113 A1 | 1/2004 | Jozefiak et al. |

(Continued)

FOREIGN PATENT DOCUMENTS

| | | |
|---|---|---|
| EP | 0682020 A1 | 11/1995 |
| WO | WO-9838859 A1 | 9/1998 |

(Continued)

OTHER PUBLICATIONS

Joharapurkar et al., 2014, http://www.ncbi.nlm.nih.gov/pmc/articles/PMC3944999/.*
Childhood-Obesity, 2015, http://michronicleonline.com/2015/06/25/childhood-obesity-why-it-exists-and-how-it-can-be-eliminated/.*
MetAp2, 2016, http://www.news-medical.net/news/20100628/Data-on-MetAP2-inhibitors-for-treatment-of-obesity-presented-at-ADA-2010.aspx.*
International Search Report and Written Opinion for International Application No. PCT/US2013/021914, mailed Apr. 23, 2013, 12 pages.

(Continued)

*Primary Examiner* — Sun Jae Yoo
(74) *Attorney, Agent, or Firm* — Goodwin Procter LLP

(57) ABSTRACT

The invention provides tricyclic sulfone compounds and their use in treating medical disorders, such as obesity. Pharmaceutical compositions and methods of making various tricyclic compounds are provided. The compounds are contemplated to have activity against methionyl aminopeptidase 2.

23 Claims, No Drawings

(56) References Cited

U.S. PATENT DOCUMENTS

| | | |
|---|---|---|
| 2004/0067266 A1 | 4/2004 | Toppo |
| 2004/0068012 A1 | 4/2004 | Comess et al. |
| 2004/0116495 A1 | 6/2004 | Marino, Jr. et al. |
| 2004/0157836 A1 | 8/2004 | Comess et al. |
| 2004/0167128 A1 | 8/2004 | Comess et al. |
| 2004/0204472 A1 | 10/2004 | Briggs et al. |
| 2005/0037994 A1 | 2/2005 | Kim et al. |
| 2005/0239878 A1 | 10/2005 | Thompson et al. |
| 2006/0045865 A1 | 3/2006 | Jacob et al. |
| 2006/0069161 A1 | 3/2006 | Lee et al. |
| 2006/0276512 A1 | 12/2006 | Han et al. |
| 2007/0078172 A1 | 4/2007 | McElroy et al. |
| 2008/0200402 A1 | 8/2008 | Alvinerie et al. |
| 2008/0312231 A1 | 12/2008 | Merla et al. |
| 2009/0088437 A1 | 4/2009 | Xie et al. |
| 2009/0148396 A1 | 6/2009 | Akullian et al. |
| 2010/0016425 A1 | 1/2010 | Vath |
| 2010/0111894 A1 | 5/2010 | Benny-Ratsaby et al. |
| 2010/0158855 A1 | 6/2010 | Benny-Ratsaby et al. |
| 2012/0004162 A1 | 1/2012 | Vath |
| 2012/0010259 A1 | 1/2012 | Vath |
| 2012/0010290 A1 | 1/2012 | Vath |
| 2013/0123235 A1 | 5/2013 | Clark et al. |
| 2013/0217759 A1 | 8/2013 | Zahler et al. |
| 2014/0073623 A1 | 3/2014 | Cramp et al. |
| 2014/0080822 A1 | 3/2014 | Cramp et al. |
| 2014/0088078 A1 | 3/2014 | Cramp et al. |
| 2015/0284369 A1 | 10/2015 | Pallin et al. |
| 2016/0083362 A1 | 3/2016 | Pallin et al. |

FOREIGN PATENT DOCUMENTS

| | | |
|---|---|---|
| WO | WO-99/57097 A2 | 11/1999 |
| WO | WO-99/59986 A1 | 11/1999 |
| WO | WO-99/59987 A1 | 11/1999 |
| WO | WO-00/64876 A1 | 11/2000 |
| WO | WO-01/24796 A1 | 4/2001 |
| WO | WO-02/26782 A2 | 4/2002 |
| WO | WO-02/059124 A2 | 8/2002 |
| WO | WO-02/083065 A2 | 10/2002 |
| WO | WO-03/027104 A1 | 4/2003 |
| WO | WO-2004/033419 A1 | 4/2004 |
| WO | WO-2005/025554 A2 | 3/2005 |
| WO | WO-2005/082349 A1 | 9/2005 |
| WO | WO-2005/113513 A2 | 12/2005 |
| WO | WO-2006/080591 A1 | 8/2006 |
| WO | WO-2008/008374 A2 | 1/2008 |
| WO | WO-2008/131947 A1 | 11/2008 |
| WO | WO-2009/009501 A2 | 1/2009 |
| WO | WO-2009/073445 A2 | 6/2009 |
| WO | WO-2010/042163 A2 | 4/2010 |
| WO | WO-2010/048499 A1 | 4/2010 |
| WO | WO-2010/065877 A2 | 6/2010 |
| WO | WO-2010/065879 A2 | 6/2010 |
| WO | WO-2010/065881 A2 | 6/2010 |
| WO | WO-2010/065883 A2 | 6/2010 |
| WO | WO-2010065877 A2 | 6/2010 |
| WO | WO-2011/044506 A2 | 4/2011 |
| WO | WO-2011/085198 A1 | 7/2011 |
| WO | WO-2011/088055 A2 | 7/2011 |
| WO | WO-2011/150338 A1 | 12/2011 |
| WO | WO-2012/012642 A1 | 1/2012 |
| WO | WO-2012/012645 A1 | 1/2012 |
| WO | WO-2012/036789 A1 | 3/2012 |
| WO | WO-2012/051318 A1 | 4/2012 |
| WO | WO-2012/064838 A1 | 5/2012 |
| WO | WO-2012/064928 A1 | 5/2012 |
| WO | WO-2012/074968 A1 | 6/2012 |
| WO | WO-2012/103333 A1 | 8/2012 |
| WO | WO-2012/154678 A1 | 11/2012 |
| WO | WO-2012/154679 A1 | 11/2012 |
| WO | WO-2013/033430 A1 | 3/2013 |

OTHER PUBLICATIONS

Wang et al. "Lead optimization of methionine aminopeptidase-2 (MetAP2) inhibitors containing sulfonamides of 5,6-disubstituted anthranilic acids" *Bioorg Med Chem Lett.* May 15, 2007;17(10):2817-22. Epub Feb. 25, 2007.

Anderson, "The Use of Fumagillin in Amoebiasis" Ann N Y Acad Sci. Dec. 30, 1952;55(6):1118-24.

Benny et al., "An Orally Delivered Small-Molecule Formulation with Antiangiogenic and Anticancer Activity" *Nat Biotechnol.* Jul. 2008;26(7):799-807. doi: 10.1038/nbt1415. Epub Jun. 29, 2008.

Bernier et al., "Fumagillin class inhibitors of methionine aminopeptidase-2" Drugs of the Future 30(5):497-500, 2005.

Brakenhielm et al., "Angiogenesis Inhibitor, TNP-470, Prevents Diet-Induced and Genetic Obesity in Mice" Circulation Research, http://circres.ahajournals.org (accessed on Feb. 8, 2007), 2004.

Braunwald et al, "Obesity" in Harrison's Principles of Internal Medicine, 15th Ed., McGraw Hill (new York) pp. 479-486, 2001.

Chan et al. "Discovery of thiophene-2-carboxylic acids as potent inhibitors of HCV NS5B polymerase and HCV subgenomic RNA replication. Part 1: Sulfonamides", Bioorg Med Chem Lett. Feb. 9, 2004;14(3):793-6.

Chun et al. "Novel inhibitors targeted to methionine aminopeptidase 2 (MetAP2) strongly inhibit the growth of cancers in xenografted nude model" Int J Cancer. Mar. 10, 2005;114(1):124-30.

Database Registry [Online] (Apr. 18, 2001), Chemical Abstracts Service, XP002664465.

Database Registry [Online] (Nov. 10, 2004), Chemical Abstracts Service, XP002664464.

Database Registry [Online] (Apr. 13, 2007), Chemical Abstracts Service, XP002664462.

Database Registry [Online] (Aug. 24, 2008), Chemical Abstracts Service, XP002664461.

Database Registry [Online] (Jan. 20, 2009), Chemical Abstracts Service, XP002664460.

Database Registry [Online] (Jan. 23, 2009), Chemical Abstracts Service, XP002664459.

Database Registry [Online] (Jan. 27, 2009), Chemical Abstracts Service, XP002664458.

Database Registry [Online] (Jan. 28, 2009), Chemical Abstracts Service, XP002664457.

Database Registry [Online] (Sep. 15, 2009), Chemical Abstracts Service, XP002664454.

Database Registry [Online], (Sep. 11, 2009) Chemical Abstracts Service, XP002664455.

Database Registry [Online], (Oct. 4, 2010) Chemical Abstracts Service, XP002664453.

Database Registry [Online} (Jun. 7, 2009), Chemical Abstracts Service, XP002664456.

Database Regsitry [Online] (Mar. 13, 2007), Chemical Abstracts Service, XP002664463.

Didier et al. "Antimicrosporidial Activities of Fumagillin, TNP-470, Ovalicin, and Ovalicin Derivatives in Vitro and In Vivo" Antimicrob Agents Chemother. Jun. 2006;50(6):2146-55.

DiPaolo et al. "Studies on the Carcinolytic Activity of Fumagillin and Some of its Derivatives," Antibiot Annu. 1958-1959;6:541-6.

Drevs et al. "Antiangiogenic Potency of FK866/K22.175, a New Inhibitor of Intracellular NAD Biosynthesis, In Murine Renal Cell Carcinoma" Anticancer Res. Nov.-Dec. 2003;23(6C):4853-8.

Dumas et al., "Synthesis and Structure Activity Relationships of Novel Small Molecule Cathepsin D Inhibitors" Bioorg Med Chem Lett. Sep. 6, 1999;9(17):2531-6.

Eder et al., "Phase 1 Dose Escalation Safety & Tolerance Study of PPI-2458 in Subjects with Non-Hodgkin's Lymphoma or Solid Tumors" (Presented on Nov. 7-10, 2006 at EORTC-NCI-AACR Symposium on "Molecular Targets and Cancer Therapeutics.") 2006.

European Search Report for EP 09798793 dated Oct. 11, 2011, 9 pages.

Everhart "Contributions of Obesity and Weight Loss to Gallstone Disease" Ann Intern Med. Nov. 15, 1993;119(10):1029-35.

Garrabrant et al. "Small molecule inhibitors of methionine aminopeptidase type 2 (MetAP-2) fail to inhibit endothelial cell proliferation or formation of microvessels from rat aortic rings in vitro" Angiogenesis. 2004;7(2):91-6.

(56) References Cited

OTHER PUBLICATIONS

Han et al. "Design and Synthesis of Highly Potent Fumagillin Analogues from Homology Modeling for a Human MetAP-2" Bioorg Med Chem Lett. Jan. 3, 2000;10(1):39-43.
Hughes et al. "Ascending dose-controlled trial of beloranib, a novel obesity treatment for safety, tolerability, and weight loss in obese women" Obesity (Silver Spring). Sep. 2013;21(9):1782-8. doi: 10.1002/oby.20356. Epub May 25, 2013.
Ingber et al. "Synthetic analogues of fumagillin that inhibit angiogenesis and suppress tumour growth" Nature. Dec. 6, 1990;348(6301):555-7.
International Search Report and Written Opinion for International Application No. PCT/US2011/044864, mailed on Oct. 7, 2011, 7 pages.
International Search Report and Written Opinion for International Application No. PCT/US2011/055987, mailed Jan. 16, 2012, 24 pages.
International Search Report and Written Opinion for International Application No. PCT/US2013/021914, mailed Apr. 18, 2013, 12 pages.
International Search Report and Written Opinion for International Application No. PCT/US2013/021919, mailed Mar. 25, 2013, 14 pages.
International Search Report and Written opinion for International Application No. PCT/US2010/052050, mailed Mar. 25, 2011, 11 pages.
International Search Report and Written Opinion for International Application No. PCT/US2012/022721, mailed on Mar. 29, 2012, 3 pages.
International Search Report for International Application No. PCT/US2012/036789, mailed Jul. 17, 2012, 4 pages.
International Search Report for International Application No. PCT/US2012/036792, mailed on Jun. 27, 2012, 3 pages.
International Search Report for International Application No. PCT/US2012/036793, mailed on Jun. 21, 2012, 4 pages.
Jeong et al, "Total synthesis and antiangiogenic activity of cyclopentane analogues of fumagillol" Bioorg Med Chem Lett. Aug. 1, 2005;15(15):3580-3.
Kawai et al. "Development of sulfonamide compounds as potent methionine aminopeptidase type II inhibiotrs with antiproliferative properties", Bioorg Med Chem Lett. Jul. 1, 2006;16(13):3574-7. Epub May 2, 2006.
Kim et al. "Assessment of the Anti-Obesity Effects of the TNP-470 Analog, CKD-732" J Mol Endocrinol. Apr. 2007;38(4):455-65.
Kim et al. "Development of parenteral formulation for a novel angiogenesis inhibitor, CKD-732 through complexation with hydroxwropyl-beta-cyclodextrin" Int J Pharm. Mar. 19, 2004;272(1-2):79-89.
Kim et al. "General pharmacology of CKD-732, a new anticancer agent: effects on central nervous, cardiovascular, and respiratory system" Biol Pharm Bull. Feb. 2005;28(2):217-23.
Kruger, "TNP-470: An Angiogenesis Inhibitor in Clinical Development for Cancer" Expert Opin Investig Drugs. Jun. 2000;9(6):1383-96.
Lee et al. "Absorption, distribution, metabolism, and excretion of CKD-732, a novel antiangiogenic fumagillin derivative, in rats, mice, and dogs" Arch Pharm Res. Feb. 2004;27(2):265-72.
Lee et al. "Design, Synthesis, and Antiangiogenic Effects of a Series of Potent Novel Fumagillin Analogues" Chem Pharm Bull (Tokyo). Jul. 2007;55(7):1024-9.
Lee et al. "Selective N-demethylation of tertiary aminofumagillols with selenium dioxide via a non-classical Polonovski type reaction" *Heterocycles* 68(5):915-932, 2006.
Lijnen et al. "Fumagillin Reduces Adipose Tissue Formation in Murine Models of Nutritionally Induced Obesity" Obesity (Silver Spring). Dec. 2010;18(12):2241-6. doi: 10.1038/oby.2009.503. Epub Jan. 21, 2010.
Makosza et al. "Reaction of organic anions. 131. Vicarious nucleophilic substitution of hydrogen in nitrobenzoic acids" Makosza, M.; Ludwiczak, S. Dep. Chem., Tech. Univ. Warsaw,
Warsaw, Pol. Synthesis (1986), (1), 50-2. CODEN: SYNTBF ISSN: 0039-7881. Journal written in English. CAN 105:171971 AN 1986:571971 CAPLUS (Copyright (C) 2009 ACS on SciFinder (R)).
Masiero et al. "New Anti-angiogenesis Agents: Review of the Clinical Experience with Carboxyamido-Triazole (CAI), Thalidomide, TNP-470 and Interleukin-12" Angiogenesis. 1997;1(1):23-35.
McCowen et al., "Fumagillin (H-3), a New Antibiotic with Amebicidal Properties" Science. Feb. 23, 1951;113(2930):202-3.
Milkowski, Deborah M., et al., Antiangiogenic Agents in Cancer Therapy, Chapter 22 "TNP-470," pp. 385-398, 2012.
Molina et al. "Potential Efficacy of Fumagillin in Intestinal Microsporidiosis Due to Enterocytozoon Bieneusi in Patients with HIV Infection: Results of a Drug Screening Study" AIDS. Nov. 1997;11(13):1603-10.
Molina et al. "Fumagillin Treatment of Intestinal Microsporidiosis" N Engl J Med. Jun. 20, 2002;346(25):1963-9.
Molina, et al. "Trial of Oral Fumagillin for the Treatment of Intestinal Microsporidiosis in Patients with HIV Infection" AIDS. Jul. 7, 2000;14(10):1341-8.
Myung et al. "The identification of in vitro metabolites of CKD-732 by liquid chromatography/tandem mass spectrometry" Rapid Commun Mass Spectrom. 2002;16(21):2048-53.
Naganuma et al. "Metronomic doxifluridine chemotherapy combined with the anti-angiogenic agent TNP-470 inhibits the growth of human uterine carcinosarcoma xenografts" Cancer Sci. Aug. 2011;102(8):1545-52. doi: 10.1111/j.1349-7006.2011.01998.x. Epub Jul. 3, 2011.
National Task Force on the Prevention and Treatment of Obesity "Very low-calorie diets. National Task Force on the Prevention and Treatment of Obesity, National Institutes of Health" JAMA. Aug. 25, 1993;270(8):967-74.
Noel et al. "Increased Risk of Acute Pancreatitis and Biliary Disease Observed in Patients with Type 2 Diabetes" Diabetes Care. May 2009;32(5):834-8. doi: 10.2337/dc08-1755. Epub Feb. 10, 2009.
Pagliarulo et al. "Gallstone disease and related risk factors in a large cohort of diabetic patients" Dig Liver Dis. Feb. 2004;36(2):130-4.
Patra et al., "Regiospecific Synthesis of Benzo[b]fluorenones via Ring Contraction by Benzil-Benzilic Acid Rearrangement of Benz[a]anthracene-5,6-diones" Synthesis 2006, (15), 2556-2562.
Picoul et al. "Progress in fumagillin synthesis" *Pure Appl. Chem.* 75(2-3): 235-249, 2003.
Rhee et al. "Angiogenesis inhibitor attenuates parathyroid hormone-induced anabolic effect" Biomed Pharmacother. Jan. 2009;63(1):63-8. doi: 10.1016/j.biopha.2007.10.013. Epub Nov. 20, 2007.
Rupnick "Adipose Tissue Mass Can be Regulated Through the Vasculature" Proc Natl Acad Sci U S A. Aug. 6, 2002;99(16):10730-5. Epub Jul. 29, 2002.
Sankar et al., "2-[1-(Phenylsulfonyl)ethyl]benzoic acid and 2-[1-(phenylsulfonyl)propyl]benzoic acid" Acta Crystallogr C. May 2002;58(Pt 5):o257-9. Epub Apr. 11, 2002.
Seneca et al. "Amebiasis: a review. II. Laboratory diagnosis, differential diagnosis and therapy" Am J Dig Dis. Jul. 1956;1(7):310-22.
Sheppard et al., "3-Amino-2-hydroxyamides and related compounds as inhibitors of methionine aminopeptidase-2" Bioorg Med Chem Lett. Feb. 23, 2004;14(4):865-8.
Sheppard et al., "Discovery and Optimization of Anthranilic Acid Sulfonamides as Inhibitors of Methionine Aminopeptidase-2: A Structural Basis for the Reduction of Albumin Binding" J Med Chem. Jun. 29, 2006;49(13):3832-49.
Shin et al. "A Phase lb pharmacokinetic study of the anti-angiogenic agent CKD-732 used in combination with capecitabine and oxaliplatin (XELOX) in metastatic colorectal cancer patients who progressed on irinotecan-based chemotherapy" Invest New Drugs. Apr. 2012;30(2):672-80.
Shin, "A Phase I Pharmacokinetic and Pharmacodynamic Stdy of CKD-732, an Antiangiogenic Agent, in Patients with Refractory Solid Cancer" Invest New Drugs. Oct. 2010;28(5):650-8.
Shvedov et al., "Functional Derivatives of Thiophene" Chemistry of Heterocyclic Compounds Feb. 1977, vol. 13, Issue 2, pp. 163-165.

(56) References Cited

OTHER PUBLICATIONS

Siddiqui et al., "The Presence of Substituents on the Aryl Moiety of the Aryl Phosphoramidate Derivative of d4T Enhances Anti-HIV Efficacy in Cell Culture: A Structure-Activity Relationship" J Med Chem. <http://www.ncbi.nlm.nih.gov/pubmed/9986709> Feb. 11, 1999;42(3):393-9.
Srikumar et al. "Structural insights on Brugia malayi transglutaminase with cinnamoyl derivatives—a molecular docking approach" *International Journal of Pharma and Bio Sciences* 3(3):998-1006, 2012.
Teicher, et al (1999) "Antiangiogenic Agents in Cancer Therapy" pp. 385-398.
Thirumamagal, et al., "Formation of 2-arylindane-1,3-diones and 3-alkylphthalides from methyl o-[?-phenylsulfonyl]toluate" Tetrahedron Letters (2008), 49(3), 512-515.
Wang et al. "Correlation of tumor growth suppression and methionine aminopetidase-2 activity blockade using an orally active inhibitor" Proc Natl Acad Sci U S A. <http://www.ncbi.nlm.nih.gov/pubmed/?term=Wang+et+al.+Correlation+of+Tumor+Growth+Suppressionand+Methionine+Aminopetidase-2> Feb. 12, 2008;105(6):1838-43. doi: 10.1073/pnas.0708766105. Epub Feb. 5, 2008.
Wang, et al., "Lead optimization of methionine aminopeptidase-2 (MetAP2) inhibitors containing sulfonamides of 5, 6-disubstituted anthranilic acids" Bioorg Med Chem Lett. May 15, 2007;17(10):2817-22. Epub Feb. 25, 2007.
Wang, et al., "Tumor Suppression by a Rationally Designed Reversible Inhibitor of Methionine Aminopeptidase-2" Cancer Res. Nov. 15, 2003;63(22):7861-9.
Weinsier et al. "Gallstone Formation and Weight Loss" Obes Res. Jan. 1993;1(1):51-6.
Weinsier et al. "Medically Safe Rate of Weight Loss for the Treatment of Obesity: A Guideline Based on Risk of Gallstone Formation" Am J Med. Feb. 1995;98(2):115-7.
Winter et al. "Endothelial anb3 Integrin-Targeted Fumagillin Nanoparticles Inhibit Angiogenesis in Atherosclerosis" Arterioscler Thromb Vasc Biol. Sep. 2006;26(9):2103-9. Epub Jul. 6, 2006.
Written Opinion of the International Searching Authority for International Application No. PCT/US2009/066811, mailed on Sep. 1, 2010, 3 pages.
Yanai et al. "Antitumor Effect of Arterial Administration of a Medium-Chain Triglyceride Solutionof an Angiogenesis Inhibitor, TNP-470, in Rabbits Bearing VX-2 Carcinoma" Pharm Res. May 1995;12(5):653-7.
Yanai et al., "Antitumor activity of a medium-chain triglyceride solution of the angiogenesis inhibitor TNP-470 (AGM-1470) when administered via the hepatic artery to rats bearing Walker 256 carcinosarcoma in the liver" J Pharmacol Exp Ther. Dec. 1994;271(3):1267-73.

\* cited by examiner

TRICYCLIC SULFONE COMPOUNDS AND METHODS OF MAKING AND USING SAME

RELATED APPLICATIONS

This application is the United States ("U.S.") National Stage of International Application No. PCT/US2013/021914, filed Jan. 17, 2013, which claims the benefit of U.S. Provisional Application No. 61/587,825, filed Jan. 18, 2012, each of which is hereby incorporated by reference in its entirety.

BACKGROUND

Over 1.1 billion people worldwide are reported to be overweight. Obesity is estimated to affect over 90 million people in the United States alone. Twenty-five percent of the population in the United States over the age of twenty is considered clinically obese. While being overweight or obese presents problems (for example restriction of mobility, discomfort in tight spaces such as theater or airplane seats, social difficulties, etc.), these conditions, in particular clinical obesity, affect other aspects of health, i.e., diseases and other adverse health conditions associated with, exacerbated by, or precipitated by being overweight or obese. The estimated mortality from obesity-related conditions in the United States is over 300,000 annually (O'Brien et al. Amer J Surgery (2002) 184:4 S-8S; and Hill et al. (1998) Science, 280:1371).

There is no curative treatment for being overweight or obese. Traditional pharmacotherapies for treating an overweight or obese subject, such as serotonin and noradrenergic re-uptake inhibitors, noradrenergic re-uptake inhibitors, selective serotonin re-uptake inhibitors, intestinal lipase inhibitors, or surgeries such as stomach stapling or gastric banding, have been shown to provide minimal short-term benefits or significant rates of relapse, and have further shown harmful side-effects to patients.

MetAP2 encodes a protein that functions at least in part by enzymatically removing the amino terminal methionine residue from certain newly translated proteins such as glyceraldehyde-3-phosphate dehydrogenase (Warder et al. (2008) J Proteome Res 7:4807). Increased expression of the MetAP2 gene has been historically associated with various forms of cancer. Molecules inhibiting the enzymatic activity of MetAP2 have been identified and have been explored for their utility in the treatment of various tumor types (Wang et al. (2003) Cancer Res. 63:7861) and infectious diseases such as microsporidiosis, leishmaniasis, and malaria (Zhang et al. (2002) J. Biomed. Sci. 9:34). Notably, inhibition of MetAP2 activity in obese and obese-diabetic animals leads to a reduction in body weight in part by increasing the oxidation of fat and in part by reducing the consumption of food (Rupnick et al. (2002) Proc. Natl. Acad. Sci. USA 99:10730).

Such MetAP2 inhibitors may be useful as well for patients with excess adiposity and conditions related to adiposity including type 2 diabetes, hepatic steatosis, and cardiovascular disease (via e.g. ameliorating insulin resistance, reducing hepatic lipid content, and reducing cardiac workload). Accordingly, compounds capable of modulating MetAP2 are needed to address the treatment of obesity and related diseases as well as other ailments favorably responsive to MetAP2 modulator treatment.

SUMMARY

The invention provides, for example, compounds which may be modulators of MetAP2, and their use as medicinal agents, processes for their preparation, and pharmaceutical compositions containing them as an active ingredient both alone or in combination with other agents, as well as provides for their use as medicaments and/or in the manufacture of medicaments for the inhibition of MetAP2 activity in warm-blooded animals such as humans. In particular this invention relates to compounds useful for the treatment of obesity, type 2 diabetes, and other obesity-associated conditions. Also provided are pharmaceutical compositions comprising at least one disclosed compound and a pharmaceutically acceptable carrier.

In an embodiment, provided herein are compounds represented by formula I:

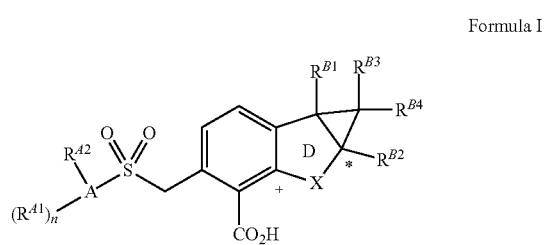

Formula I or pharmaceutically acceptable salts, stereoisomers, esters or prodrugs thereof, where A, D, $R^{A1}$, $R^{A2}$, $R^{B1}$, $R^{B2}$, $R^{B3}$, $R^{B4}$, X, and n are as defined herein.

DETAILED DESCRIPTION

The features and other details of the disclosure will now be more particularly described. Before further description of the present invention, certain terms employed in the specification, examples and appended claims are collected here. These definitions should be read in light of the remainder of the disclosure and as understood by a person of skill in the art. Unless defined otherwise, all technical and scientific terms used herein have the same meaning as commonly understood by a person of ordinary skill in the art.

DEFINITIONS

"Treating" includes any effect, e.g., lessening, reducing, modulating, or eliminating, that results in the improvement of the condition, disease, disorder and the like.

The term "alkenyl" as used herein refers to an unsaturated straight or branched hydrocarbon having at least one carbon-carbon double bond. Exemplary alkenyl groups include, but are not limited to, a straight or branched group of 2-6 or 3-4 carbon atoms, referred to herein as $C_{2-6}$alkenyl, and $C_{3-4}$alkenyl, respectively. Exemplary alkenyl groups include, but are not limited to, vinyl, allyl, butenyl, pentenyl, etc.

The term "alkoxy" as used herein refers to a straight or branched alkyl group attached to oxygen (alkyl-O—). Exemplary alkoxy groups include, but are not limited to, alkoxy groups of 1-6 or 2-6 carbon atoms, referred to herein as $C_{1-6}$alkoxy, and $C_{2-6}$alkoxy, respectively. Exemplary alkoxy groups include, but are not limited to methoxy, ethoxy, isopropoxy, etc.

The term "alkoxyalkyl" as used herein refers to a straight or branched alkyl group attached to oxygen, attached to a second straight or branched alkyl group (alkyl-O-alkyl-). Exemplary alkoxyalkyl groups include, but are not limited to, alkoxyalkyl groups in which each of the alkyl groups independently contains 1-6 carbon atoms, referred to herein as $C_{1-6}$alkoxy-$C_{1-6}$alkyl. Exemplary alkoxyalkyl groups include, but are not limited to methoxymethyl, 2-methoxyethyl, 1-methoxyethyl, 2-methoxypropyl, ethoxymethyl, 2-isopropoxyethyl etc.

The term "alkyoxycarbonyl" as used herein refers to a straight or branched alkyl group attached to oxygen, attached to a carbonyl group (alkyl-O—C(O)—). Exemplary alkoxycarbonyl groups include, but are not limited to, alkoxycarbonyl groups of 1-6 carbon atoms, referred to herein as $C_{1-6}$alkoxycarbonyl. Exemplary alkoxycarbonyl groups include, but are not limited to, methoxycarbonyl, ethoxycarbonyl, t-butoxycarbonyl, etc.

The term "alkenyloxy" used herein refers to a straight or branched alkenyl group attached to oxygen (alkenyl-O—). Exemplary alkenyloxy groups include, but are not limited to, groups with an alkenyl group of 3-6 carbon atoms, referred to herein as $C_{3-6}$alkenyloxy. Exemplary "alkenyloxy" groups include, but are not limited to allyloxy, butenyloxy, etc.

The term "alkynyloxy" used herein refers to a straight or branched alkynyl group attached to oxygen (alkynyl-O). Exemplary alkynyloxy groups include, but are not limited to, groups with an alkynyl group of 3-6 carbon atoms, referred to herein as $C_{3-6}$alkynyloxy. Exemplary alkynyloxy groups include, but are not limited to, propynyloxy, butynyloxy, etc.

The term "alkyl" as used herein refers to a saturated straight or branched hydrocarbon. Exemplary alkyl groups include, but are not limited to, straight or branched hydrocarbons of 1-6, 1-4, or 1-3 carbon atoms, referred to herein as $C_{1-6}$alkyl, $C_{1-4}$alkyl, and $C_{1-3}$alkyl, respectively. Exemplary alkyl groups include, but are not limited to, methyl, ethyl, propyl, isopropyl, 2-methyl-1-butyl, 3-methyl-2-butyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, etc.

The term "alkylcarbonyl" as used herein refers to a straight or branched alkyl group attached to a carbonyl group (alkyl-C(O)—). Exemplary alkylcarbonyl groups include, but are not limited to, alkylcarbonyl groups of 1-6 atoms, referred to herein as $C_{1-6}$alkylcarbonyl groups. Exemplary alkylcarbonyl groups include, but are not limited to, acetyl, propanoyl, isopropanoyl, butanoyl, etc.

The term "alkynyl" as used herein refers to an unsaturated straight or branched hydrocarbon having at least one carbon-carbon triple bond. Exemplary alkynyl groups include, but are not limited to, straight or branched groups of 2-6, or 3-6 carbon atoms, referred to herein as $C_{2-6}$alkynyl, and $C_{3-6}$alkynyl, respectively. Exemplary alkynyl groups include, but are not limited to, ethynyl, propynyl, butynyl, pentynyl, hexynyl, methylpropynyl, etc.

The term "carbonyl" as used herein refers to the radical —C(O)—.

The term "cyano" as used herein refers to the radical —CN.

The term "cycloalkoxy" as used herein refers to a cycloalkyl group attached to oxygen (cycloalkyl-O—). Exemplary cycloalkoxy groups include, but are not limited to, cycloalkoxy groups of 3-6 carbon atoms, referred to herein as $C_{3-6}$cycloalkoxy groups. Exemplary cycloalkoxy groups include, but are not limited to, cyclopropoxy, cyclobutoxy, cyclohexyloxy, etc The terms "cycloalkyl" or a "carbocyclic group" as used herein refers to a saturated or partially unsaturated hydrocarbon group of, for example, 3-6, or 4-6 carbons, referred to herein as $C_{3-6}$cycloalkyl or $C_{4-6}$cycloalkyl, respectively. Exemplary cycloalkyl groups include, but are not limited to, cyclohexyl, cyclopentyl, cyclopentenyl, cyclobutyl or cyclopropyl.

The terms "halo" or "halogen" as used herein refer to F, Cl, Br, or I.

The terms "heteroaryl" or "heteroaromatic group" as used herein refers to a monocyclic aromatic 5-6 membered ring system containing one or more heteroatoms, for example one to three heteroatoms, such as nitrogen, oxygen, and sulfur. Where possible, said heteroaryl ring may be linked to the adjacent radical though carbon or nitrogen. Examples of heteroaryl rings include but are not limited to furan, thiophene, pyrrole, thiazole, oxazole, isothiazole, isoxazole, imidazole, pyrazole, triazole, pyridine or pyrimidine etc.

The terms "heterocyclyl" or "heterocyclic group" are art-recognized and refer to saturated or partially unsaturated 4-7 membered ring structures, whose ring structures include one to three heteroatoms, such as nitrogen, oxygen, and sulfur. Where possible, heterocyclyl rings may be linked to the adjacent radical through carbon or nitrogen. Examples of heterocyclyl groups include, but are not limited to, pyrrolidine, piperidine, morpholine, thiomorpholine, piperazine, oxetane, azetidine, tetrahydrofuran or dihydrofuran etc.

The term "heterocyclyloxy" as used herein refers to a heterocyclyl group attached to oxygen (heterocyclyl-O—).

The term "heteroaryloxy" as used herein refers to a heteroaryl group attached to oxygen (heteroaryl-O—).

The terms "hydroxy" and "hydroxyl" as used herein refers to the radical —OH.

The term "oxo" as used herein refers to the radical =O.

"Pharmaceutically or pharmacologically acceptable" include molecular entities and compositions that do not produce an adverse, allergic or other untoward reaction when administered to an animal, or a human, as appropriate. For human administration, preparations should meet sterility, pyrogenicity, and general safety and purity standards as required by FDA Office of Biologics standards.

The term "pharmaceutically acceptable carrier" or "pharmaceutically acceptable excipient" as used herein refers to any and all solvents, dispersion media, coatings, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions.

The term "pharmaceutical composition" as used herein refers to a composition comprising at least one compound as disclosed herein formulated together with one or more pharmaceutically acceptable carriers.

"Individual," "patient," or "subject" are used interchangeably and include any animal, including mammals, preferably mice, rats, other rodents, rabbits, dogs, cats, swine, cattle, sheep, horses, or primates, and most preferably humans. The compounds of the invention can be administered to a mammal, such as a human, but can also be administered to other mammals such as an animal in need of veterinary treatment, e.g., domestic animals (e.g., dogs, cats, and the like), farm animals (e.g., cows, sheep, pigs, horses, and the like) and laboratory animals (e.g., rats, mice, guinea pigs, and the like). The mammal treated in the methods of the invention is desirably a mammal in which treatment of obesity or weight loss is desired. "Modulation" includes antagonism (e.g., inhibition), agonism, partial antagonism and/or partial agonism.

In the present specification, the term "therapeutically effective amount" means the amount of the subject compound that will elicit the biological or medical response of a tissue, system or animal, (e.g. mammal or human) that is being sought by the researcher, veterinarian, medical doctor or other clinician. The compounds of the invention are administered in therapeutically effective amounts to treat a disease. Alternatively, a therapeutically effective amount of a compound is the quantity required to achieve a desired therapeutic and/or prophylactic effect, such as an amount which results in weight loss.

The term "pharmaceutically acceptable salt(s)" as used herein refers to salts of acidic or basic groups that may be present in compounds used in the compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including, but not limited to, malate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that are acidic in nature are capable of forming base salts with various pharmacologically acceptable cations. Examples of such salts include alkali metal or alkaline earth metal salts, particularly calcium, magnesium, sodium, lithium, zinc, potassium, and iron salts. Compounds included in the present compositions that include a basic or acidic moiety may also form pharmaceutically acceptable salts with various amino acids. The compounds of the disclosure may contain both acidic and basic groups; for example, one amino and one carboxylic acid group. In such a case, the compound can exist as an acid addition salt, a zwitterion, or a base salt.

The compounds of the disclosure may contain one or more chiral centers and, therefore, exist as stereoisomers. The term "stereoisomers" when used herein consist of all enantiomers or diastereomers. These compounds may be designated by the symbols "(+)," "(−)," "R" or "S," depending on the configuration of substituents around the stereogenic carbon atom, but the skilled artisan will recognize that a structure may denote a chiral center implicitly. The present invention encompasses various stereoisomers of these compounds and mixtures thereof. Mixtures of enantiomers or diastereomers may be designated "(±)" in nomenclature, but the skilled artisan will recognize that a structure may denote a chiral center implicitly.

The compounds of the disclosure may contain one or more double bonds and, therefore, exist as geometric isomers resulting from the arrangement of substituents around a carbon-carbon double bond. The symbol ═ denotes a bond that may be a single, double or triple bond as described herein. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers. Substituents around a carbon-carbon double bond alternatively can be referred to as "cis" or "trans," where "cis" represents substituents on the same side of the double bond and "trans" represents substituents on opposite sides of the double bond.

Compounds of the disclosure may contain a carbocyclic or heterocyclic ring and therefore, exist as geometric isomers resulting from the arrangement of substituents around the ring. The arrangement of substituents around a carbocyclic or heterocyclic ring are designated as being in the "Z" or "E" configuration wherein the terms "Z" and "E" are used in accordance with IUPAC standards. Unless otherwise specified, structures depicting carbocyclic or heterocyclic rings encompass both "Z" and "E" isomers. Substituents around a carbocyclic or heterocyclic rings may also be referred to as "cis" or "trans", where the term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans."

Individual enantiomers and diasteriomers of compounds of the present invention can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, (3) direct separation of the mixture of optical enantiomers on chiral liquid chromatographic columns or (4) kinetic resolution using stereoselective chemical or enzymatic reagents. Racemic mixtures can also be resolved into their component enantiomers by well known methods, such as chiral-phase liquid chromatography or crystallizing the compound in a chiral solvent. Stereoselective syntheses, a chemical or enzymatic reaction in which a single reactant forms an unequal mixture of stereoisomers during the creation of a new stereocenter or during the transformation of a pre-existing one, are well known in the art. Stereoselective syntheses encompass both enantio- and diastereoselective transformations, and may involve the use of chiral auxiliaries. For examples, see Carreira and Kvaerno, *Classics in Stereoselective Synthesis*, Wiley-VCH: Weinheim, 2009.

The compounds disclosed herein can exist in solvated as well as unsolvated forms with pharmaceutically acceptable solvents such as water, ethanol, and the like, and it is intended that the invention embrace both solvated and unsolvated forms. In one embodiment, the compound is amorphous. In one embodiment, the compound is a single polymorph. In another embodiment, the compound is a mixture of polymorphs. In another embodiment, the compound is in a crystalline form.

The invention also embraces isotopically labeled compounds of the invention which are identical to those recited herein, except that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, sulfur, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. For example, a compound of the invention may have one or more H atom replaced with deuterium.

Certain isotopically-labeled disclosed compounds (e.g., those labeled with $^3$H and $^{14}$C) are useful in compound and/or substrate tissue distribution assays. Tritiated (i.e., $^3$H) and carbon-14 (i.e., $^{14}$C) isotopes are particularly preferred for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Isotopically labeled compounds of the invention can generally be prepared by following procedures analogous to those disclosed in the examples herein by substituting an isotopically labeled reagent for a non-isotopically labeled reagent.

The term "prodrug" refers to compounds that are transformed in vivo to yield a disclosed compound or a pharmaceutically acceptable salt, hydrate or solvate of the compound. The transformation may occur by various mechanisms (such as by esterase, amidase, phosphatase, oxidative and or reductive metabolism) in various locations (such as in the intestinal lumen or upon transit of the intestine, blood or liver). Prodrugs are well known in the art (for example, see Rautio, Kumpulainen, et al, Nature Reviews Drug Discovery 2008, 7, 255). For example, if a compound of the invention or a pharmaceutically acceptable salt, hydrate or solvate of the compound contains a carboxylic acid functional group, a prodrug can comprise an ester formed by the replacement of the hydrogen atom of the acid group with a group such as ($C_{1-8}$)alkyl, ($C_{2-12}$)alkylcarbonyloxymethyl, 1-(alkylcarbonyloxy)ethyl having from 4 to 9 carbon atoms, 1-methyl-1-(alkylcarbonyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_{1-2}$)alkylamino($C_{2-3}$)alkyl (such as β-dimethylaminoethyl), carbamoyl-($C_{1-2}$)alkyl, N,N-di($C_{1-2}$)alkylcarbamoyl-($C_{1-2}$)alkyl and piperidino-, pyrrolidino- or morpholino($C_{2-3}$)alkyl.

Similarly, if a compound of the invention contains an alcohol functional group, a prodrug can be formed by the replacement of the hydrogen atom of the alcohol group with a group such as ($C_{1-6}$)alkylcarbonyloxymethyl, 1-(($C_{1-6}$)alkylcarbonyloxy)ethyl, 1-methyl-1-(($C_{1-6}$)alkylcarbonyloxy)ethyl($C_{1-6}$)alkoxycarbonyloxymethyl, N—($C_{1-6}$)alkoxycarbonylaminomethyl, succinoyl, ($C_{1-6}$)alkylcarbonyl, α-amino($C_{1-4}$)alkylcarbonyl, arylalkylcarbonyl and α-aminoalkylcarbonyl, or α-aminoalkylcarbonyl-α-aminoalkylcarbonyl, where each α-aminoalkylcarbonyl group is independently selected from the naturally occurring L-amino acids, P(O)(OH)$_2$, —P(O)(O($C_{1-6}$)alkyl)$_2$ or glycosyl (the radical resulting from the removal of a hydroxyl group of the hemiacetal form of a carbohydrate).

If a compound of the invention incorporates an amine functional group, a prodrug can be formed, for example, by creation of an amide or carbamate, an N-alkylcarbonyloxyalkyl derivative, an (oxodioxolenyl)methyl derivative, an N-Mannich base, imine or enamine. In addition, a secondary amine can be metabolically cleaved to generate a bioactive primary amine, or a tertiary amine can metabolically cleaved to generate a bioactive primary or secondary amine. For examples, see Simplício, et al., *Molecules* 2008, 13, 519 and references therein.

I. Tricyclic Compounds in certain embodiments, the present invention provides compounds of Formula I:

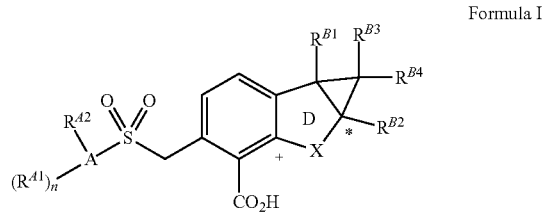

Formula I wherein

D may be a 5-7 membered heterocyclic or carbocyclic ring;

X may be selected from the group consisting of: $^+$—C($R^{D1}R^{D2}$)—C($R^{D5}R^{D6}$)—*, $^+$—$W^1$—C($R^{D5}R^{D6}$)—*, $^+$—$W^1$—C(O)—*, $^+$—C($R^{D1}R^{D2}$)—$W^3$—*, $^+$—C($R^{D1}R^{D2}$)—C($R^{D3}R^{D4}$)—C($R^{D5}R^{D6}$)—*, $^+$—$W^1$—C($R^{D3}R^{D4}$)—C($R^{D5}R^{D6}$)—*, $^+$—$W^1$—C(O)—C($R^{D5}R^{D6}$)—*, $^+$—C($R^{D1}R^{D2}$)—$W^2$—C($R^{D5}R^{D6}$)—*, $^+$—C($R^{D1}R^{D2}$)—$W^2$—C(O)—*, $^+$—C($R^{D1}R^{D2}$)—C($R^{D3}R^{D4}$)—$W^3$—*, $^+$—C($R^{D1}R^{D2}$)—C(O)—$W^3$—*, in which the attachment points are indicated by $^+$ and * in X and in Formula I;

$W^1$ may be selected from the group consisting of: O or N($R^{N1}$)

$W^2$ may be selected from the group consisting of: O or N($R^{N2}$)

$W^3$ may be selected from the group consisting of O or N($R^{N3}$)

$R^{B1}$ and $R^{B2}$ may be independently selected from the group consisting of hydrogen, fluorine, hydroxyl, CN, $C_{1-3}$alkyl or $C_{1-2}$alkoxy; wherein the $C_{1-3}$alkyl and $C_{1-2}$alkoxy groups may be optionally substituted by one or more fluorine atoms or a cyano, hydroxyl or $C_{1-2}$alkoxy group.

$R^{B3}$ and $R^{B4}$ may be independently selected from the group consisting of hydrogen, fluorine or $C_{1-2}$alkyl group; wherein the $C_{1-2}$alkyl group may be optionally substituted by one or more fluorine atoms.

A may be a ring selected from the group consisting of: phenyl, a 5-6 membered heteroaryl having 1, 2 or 3 heteroatoms each selected from S, N or O, and a 4-7 membered heterocycle having 1, 2 or 3 heteroatoms each selected from N or O;

$R^{A1}$ may be selected, independently for each occurrence, from the group consisting of: hydrogen, hydroxyl, cyano, halogen, $C_{1-4}$alkyl or $C_{1-3}$alkoxy; wherein $C_{1-4}$alkyl, or $C_{1-3}$alkoxy may be optionally substituted by one or more fluorines;

n may be 1 or 2;

$R^{A2}$ may be selected from the group consisting of: hydrogen, $R^iR^jN$—, heterocyclyl, heterocyclyloxy, heterocyclyl-(NR$^a$)—; wherein said heterocyclyl may optionally be substituted by one or more substituents selected from R$^g$ and wherein if said heterocyclyl contains a —NH moiety that nitrogen may optionally be substituted by one or more groups R$^h$; or $R^{A2}$ may be selected from the group consisting of: $C_{1-6}$alkyl, $C_{2-6}$alkenyl, $C_{2-6}$alkynyl, $C_{3-6}$cycloalkyl, $C_{1-6}$alkoxy, $C_{3-6}$alkenyloxy, $C_{3-6}$alkynyloxy, $C_{3-6}$cycloalkoxy, $C_{1-6}$alkyl-S(O)$_w$— (wherein w is 0, 1 or 2), $C_{1-6}$alkyl-N(R$^a$)—, $C_{1-6}$alkyl-N(R$^a$)-carbonyl-, $C_{1-6}$alkylcarbonyl-N(R$^a$)—, $C_{1-6}$alkyl-N(R$^a$)-carbonyl-N(R$^a$)—, $C_{1-6}$alkyl-N(R$^a$)—SO$_2$—, $C_{1-6}$alkyl-SO$_2$—N(R$^a$)—, $C_{1-6}$alkoxycarbonyl-N(R$^3$)—, $C_{1-6}$alkylcarbonyl-N(R$^a$)—$C_{1-6}$alkyl-, $C_{1-6}$alkyl-N(R$^a$)-carbonyl-$C_{1-6}$alkyl-, $C_{1-6}$alkoxyC$_{1-6}$alkyl-; wherein $C_{1-6}$alkyl, $C_{2-6}$alkenyl, $C_{2-6}$alkynyl, $C_{3-6}$cycloalkyl, $C_{1-6}$alkoxy, $C_{3-6}$alkenyloxy, $C_{3-6}$alkynyloxy, $C_{3-6}$cycloalkoxy, $C_{1-6}$alkyl-N(R$^a$)-carbonyl-, $C_{1-6}$alkylcarbonyl-N(R$^a$)—, $C_{1-6}$alkyl-N(R$^a$)-carbonyl-N(R$^a$)—, $C_{1-6}$alkyl-N(R$^a$)—SO$_2$—, $C_{1-6}$alkyl-SO$_2$—N(R$^a$)—, $C_{1-6}$alkoxycarbonyl-N(R$^a$)—, $C_{1-6}$alkylcarbonyl-N(R$^a$)C$_{1-6}$alkyl-, $C_{1-6}$alkyl-N(R$^a$)-carbonyl-$C_{1-6}$alkyl-, $C_{1-6}$alkoxy-$C_{1-6}$alkyl may optionally be substituted by R$^P$, phenyl, phenoxy, heteroaryl, heteroaryloxy, heteroaryl-(NR$^a$)—, heterocyclyl, heterocyclyloxy or heterocyclyl-N(R$^a$)—; and wherein said heteroaryl or phenyl may optionally be substituted with one or more substituents selected from R$^f$; and wherein said heterocyclyl may optionally be substituted by one or more substituents selected from R$^g$; and wherein if said heterocyclyl contains a NH moiety that nitrogen may optionally be substituted by one or more groups R$^h$;

R$^{D1}$ and R$^{D2}$ may be each independently selected from the group consisting of: hydrogen, fluorine, hydroxyl, $C_{1-2}$alkyl or $C_{1-2}$alkoxy; wherein the $C_{1-2}$alkyl and $C_{1-2}$alkoxy may optionally be substituted by one or more fluorine atoms or a group selected from cyano or hydroxyl.

R$^{D3}$ and R$^{D4}$ may be each independently selected from the group consisting of: hydrogen, fluorine, hydroxyl, cyano, $C_{1-3}$alkyl or $C_{1-3}$alkoxy; wherein the $C_{1-3}$ alkyl and $C_{1-3}$ alkoxy may optionally be substituted by one or more fluorine atoms or a group selected from cyano, hydroxyl or N(R$^a$R$^b$);

R$^{D5}$ and R$^{D6}$ may be each independently selected from the group consisting of: hydrogen, fluorine, hydroxyl, cyano, $C_{1-2}$alkyl or $C_{1-2}$alkoxy; wherein the $C_{1-2}$alkyl and $C_{1-2}$alkoxy may optionally be substituted by one or more fluorine atoms or a group selected from cyano, hydroxyl or N(R$^a$R$^b$);

R$^{N1}$ may be selected from the group consisting of: hydrogen or $C_{1-2}$alkyl;

R$^{N2}$ may be selected from the group consisting of: hydrogen, $C_{1-3}$alkyl or $C_{1-2}$alkylcarbonyl; wherein the $C_{1-3}$alkyl and $C_{1-2}$alkylcarbonyl may optionally be substituted by one or more fluorine atoms or a group selected from cyano, hydroxyl or N(R$^a$R$^b$);

R$^{N3}$ may be selected from the group consisting of hydrogen, $C_{1-3}$alkyl or $C_{1-2}$alkylcarbonyl; wherein the $C_{1-3}$alkyl and $C_{1-2}$alkylcarbonyl may optionally be substituted by one or more fluorine atoms or a group selected from cyano, hydroxyl or N(Rule);

R$^a$ and R$^b$ may be independently selected, for each occurrence, from the group consisting of: hydrogen and $C_{1-3}$alkyl; wherein $C_{1-3}$alkyl may optionally be substituted by one or more substituents selected from: fluorine, cyano, oxo and hydroxyl;

or R$^a$ and R$^b$, together with the nitrogen to which they are attached, may form a 4-6 membered heterocyclic ring which may have an additional heteroatom selected from O, S, or N; and wherein the 4-6 membered heterocyclic ring may optionally be substituted by one or more substituents selected from the group consisting of: fluorine, cyano, oxo or hydroxyl;

R$^f$ may be independently selected, for each occurrence, from the group consisting of: R$^P$, hydrogen, $C_{1-6}$alkyl, $C_{3-6}$cycloalkyl, $C_{2-6}$alkenyl, $C_{2-6}$alkynyl, $C_{3-6}$cycloalkyl, $C_{1-6}$alkoxy, $C_{1-6}$alkyl-S(O)$_w$— (wherein w is 0, 1 or 2), $C_{1-6}$alkylcarbonyl-N(R$^a$)—; $C_{1-6}$alkoxycarbonyl-N(R$^a$)—; and wherein $C_{1-6}$alkyl, $C_{3-6}$cycloalkyl, $C_{2-6}$alkenyl, $C_{2-6}$alkynyl, $C_{3-6}$cycloalkyl, $C_{1-6}$alkoxy, $C_{1-6}$alkyl-S(O)$_w$—, $C_{1-6}$alkylcarbonyl-N(R$^a$)—, $C_{1-6}$alkoxycarbonyl-N(R$^a$)— may be optionally substituted by one or more substituents selected from R$^P$;

R$^g$ may be independently selected for each occurrence from the group consisting of: R$^P$, hydrogen, oxo, $C_{1-6}$alkyl, $C_{2-6}$alkenyl, $C_{2-6}$alkynyl, $C_{3-6}$cycloalkyl, $C_{1-6}$alkoxy, (wherein w is 0, 1 or 2), $C_{1-6}$alkylcarbonyl-N(R$^a$)—, $C_{1-6}$alkoxycarbonyl-N(R$^a$)—; wherein $C_{1-6}$alkyl, $C_{2-6}$alkenyl, $C_{2-6}$alkynyl, $C_{3-6}$cycloalkyl, $C_{1-6}$alkoxy, $C_{1-6}$alkylcarbonyl-N(R$^a$)—, $C_{1-6}$alkoxycarbonyl-N(R$^a$)— may be optionally substituted by one or more substituents selected from R$^P$;

R$^h$ may be independently selected for each occurrence from the group consisting of: hydrogen, $C_{1-6}$alkyl, $C_{3-6}$alkenyl, $C_{3-6}$alkynyl, $C_{3-6}$cycloalkyl, $C_{1-6}$alkyl-S(O)$_2$—, $C_{1-6}$alkoxycarbonyl-, R$^i$R$^j$N-carbonyl-, R$^i$R$^j$N—SO$_2$—; wherein $C_{1-6}$alkyl, $C_{3-6}$alkenyl, $C_{3-6}$alkynyl, $C_{3-6}$cycloalkyl, $C_{1-6}$alkyl-S(O)$_2$—, $C_{1-6}$alkylcarbonyl- may optionally be substituted by one or more substituents selected from R$^P$;

R$^i$ and R$^j$, may be selected independently for each occurrence from the group consisting of: hydrogen, $C_{1-4}$alkyl and $C_{3-6}$cycloalkyl; wherein $C_{1-4}$alkyl and $C_{3-6}$cycloalkyl may be optionally substituted by one or more substituents selected from fluorine, hydroxyl, cyano, R$^a$R$^b$N—, R$^a$R$^b$N-carbonyl-, $C_{1-3}$alkoxy;

or R$^i$ and R$^j$ taken together with the nitrogen to which they are attached form a 4-7 membered heterocyclic ring which may have an additional heteroatom selected from O, S, or N, optionally substituted on carbon by one or more substituents selected from the group consisting of: fluorine, hydroxyl, oxo, cyano, $C_{1-6}$alkyl, $C_{1-6}$alkoxy, R$^a$R$^b$N—, R$^a$R$^b$N—SO$_2$—, R$^a$R$^b$N-carbonyl-; and wherein said $C_{1-6}$alkyl or $C_{1-6}$alkoxy may optionally be substituted by fluorine, hydroxyl or cyano; and optionally substituted on nitrogen by one or more substituents selected from the group consisting of: $C_{1-6}$alkyl, R$^a$R$^b$N-carbonyl-; and wherein said $C_{1-6}$alkyl may be optionally substituted by fluorine, hydroxyl, cyano;

R$^P$ may be independently selected, for each occurrence, from the group consisting of: halogen, hydroxyl, cyano, $C_{1-6}$alkoxy, R$^i$R$^j$N—, R$^i$R$^j$N-carbonyl-, R$^i$R$^j$N—SO$_2$—, R$^i$R$^j$N-carbonyl-N(R$^a$)—;

and pharmaceutically acceptable salts, stereoisomers, esters and prodrugs thereof.

In some embodiments, X may be selected from the group consisting of: $^+$—C(R$^{D1}$R$^{D2}$)—C(R$^{D5}$R$^{D6}$)—*, $^+$—O—C(R$^{D5}$R$^{D6}$)*, $^+$—N(R$^{N2}$)—C(R$^{D5}$R$^{D6}$)—*, and $^+$—O—C(R$^{D3}$R$^{D4}$)—C(R$^{D5}$R$^{D6}$)—*; wherein the $^+$ and * indicate the attachment points of X as indicated in Formula I. Exemplary X moieties may be selected from the group consisting of: $^+$—CH$_2$—CH$_2$—*, $^+$—O—CH$_2$—*, and $^+$—NH—CH$_2$—*; wherein the + and * indicate the attachment points of X as indicated in Formula I.

In one embodiment, R$^{D1}$, R$^{D2}$, R$^{N1}$ and R$^{N2}$ that form part of X may be independently selected from the group consisting of hydrogen and methyl. For example, R$^{D1}$, R$^{D2}$, R$^{N1}$ and R$^{N2}$ that form part of X may be hydrogen.

In certain embodiments, R$^{D3}$, R$^{D4}$, R$^{D5}$ and R$^{D6}$ that form part of X may be independently selected for each occurrence from the group consisting of hydrogen, fluorine, cyano, and $C_{1-2}$alkyl. For example, R$^{D3}$, R$^{D4}$, R$^{D5}$ and R$^{D6}$ that form part of X may be hydrogen.

In an embodiment, R$^{B1}$ and R$^{D2}$ may be independently selected from the group consisting of H and methyl.

In another embodiment, R$^{B3}$ and R$^{B4}$ may be independently selected from the group consisting of H and fluorine.

Provided herein, for example, are tricyclic compounds represented by formulas Ia, Ib, Ic, Id and Ie:

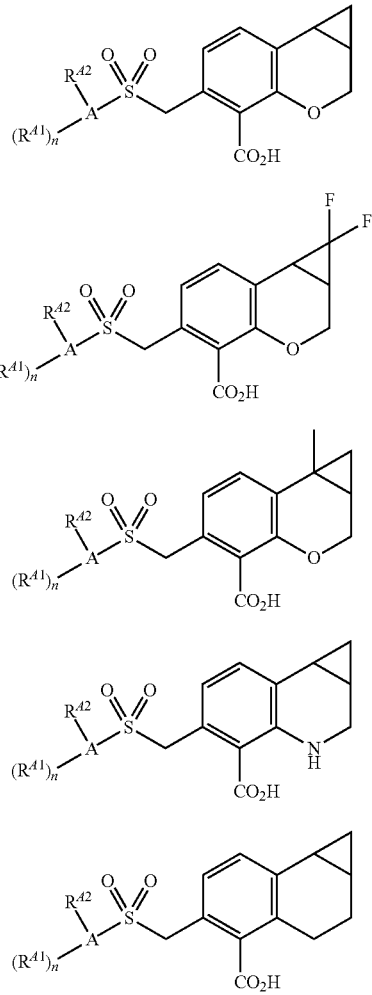

In certain embodiments, A may be phenyl.

Also provided herein is a compound represented by Formula II:

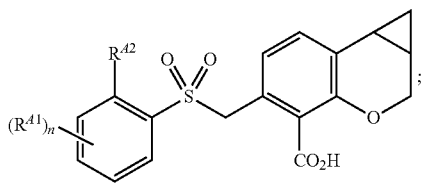

wherein:

$R^{A1}$ may be selected from the group consisting of: hydrogen, halogen, $C_{1-2}$alkyl, $C_{1-2}$alkoxy; wherein $C_{1-2}$alkyl may optionally be substituted by one or more fluorines;

$R^{A2}$ may be selected from the group consisting of: hydrogen, $R^iR^jN$, heterocyclyl, $C_{1-6}$alkyl, $C_{3-6}$alkenyl, $C_{3-6}$cycloalkyl, $C_{1-6}$alkoxy; wherein said heterocyclyl may optionally be substituted by one or more groups $R^g$, and wherein if said heterocyclyl contains a —NH moiety, that nitrogen may optionally be substituted by on or more groups $R^h$; and wherein said $C_{1-6}$alkyl, $C_{3-6}$alkenyl, $C_{3-6}$cycloalkyl and $C_{1-6}$alkoxy may optionally be substituted by one or more groups $R^P$;

n may be 1 or 2;

$R^g$ may be independently selected for each occurrence from the group consisting of: $R^P$, hydrogen, oxo, $C_{1-6}$alkyl, $C_{2-6}$alkenyl, $C_{2-6}$alkynyl, $C_{3-6}$cycloalkyl, $C_{1-6}$alkoxy, $C_{1-6}$alkyl-S(O)$_w$— (wherein w is 0, 1 or 2), $C_{1-6}$alkylcarbonyl-N(R$^a$)—, $C_{1-6}$alkoxycarbonyl-N(R$^a$)—; wherein $C_{1-6}$alkyl, $C_{2-6}$alkenyl, $C_{2-6}$alkynyl, $C_{3-6}$cycloalkyl, $C_{1-6}$alkoxy, $C_{1-6}$alkyl-S(O)$_w$—, $C_{1-6}$alkylcarbonyl-N(R$^a$)—, $C_{1-6}$alkoxycarbonyl-N(R$^a$)— may be optionally substituted by one or more substituents selected from $R^P$; $R^h$ is independently selected for each occurrence from the group consisting of: hydrogen, $C_{1-6}$alkyl, $C_{3-6}$alkenyl, $C_{3-6}$alkynyl, $C_{3-6}$cycloalkyl, $C_{1-6}$alkyl-S(O)$_2$—, $C_{1-6}$alkoxycarbonyl-, $R^iR^jN$-carbonyl-, $R^iR^jN$—SO$_2$—; wherein $C_{1-6}$alkyl, $C_{3-6}$alkenyl, $C_{3-6}$alkynyl, $C_{3-6}$cycloalkyl, $C_{1-6}$alkyl-S(O)$_2$—, $C_{1-6}$alkylcarbonyl- may optionally be substituted by one or more substituents selected from $R^P$;

$R^h$ may be independently selected for each occurrence from the group consisting of: hydrogen, $C_{1-6}$alkyl, $C_{3-6}$alkenyl, $C_{3-6}$alkynyl, $C_{3-6}$cycloalkyl, $C_{1-6}$alkyl-S(O)$_2$—, $C_{1-6}$alkoxycarbonyl-, $R^iR^jN$-carbonyl-, $R^iR^jN$—SO$_2$—; wherein $C_{1-6}$alkyl, $C_{3-6}$alkenyl, $C_{3-6}$alkynyl, $C_{3-6}$cycloalkyl, $C_{1-6}$alkyl-S(O)$_2$—, $C_{1-6}$alkylcarbonyl- may optionally be substituted by one or more substituents selected from $R^P$;

$R^i$ and $R^j$, may be selected independently for each occurrence from the group consisting of: hydrogen, $C_{1-4}$alkyl and $C_{3-6}$cycloalkyl; wherein $C_{1-4}$alkyl and $C_{3-6}$cycloalkyl may be optionally substituted by one or more substituents selected from fluorine, hydroxyl, cyano, $R^aR^bN$—, $R^aR^bN$-carbonyl-, $C_{1-3}$alkoxy;

or $R^i$ and $R^j$ taken together with the nitrogen to which they are attached form a 4-7 membered heterocyclic ring which may have an additional heteroatom selected from O, S, or N, optionally substituted on carbon by one or more substituents selected from the group consisting of: fluorine, hydroxyl, oxo, cyano, $C_{1-6}$alkyl, $C_{1-6}$-alkoxy, $R^aR^bN$—, $R^aR^bN$—SO$_2$—, $R^aR^bN$-carbonyl-; and wherein said $C_{1-6}$alkyl or $C_{1-6}$alkoxy may optionally be substituted by fluorine, hydroxyl or cyano; and optionally substituted on nitrogen by one or more substituents selected from the group consisting of: $C_{1-6}$alkyl, $R^aR^bN$-carbonyl-; and wherein said $C_{1-6}$alkyl may be optionally substituted by fluorine, hydroxyl, cyano;

$R^P$ may be independently selected, for each occurrence, from the group consisting of: halogen, hydroxyl, cyano, $C_{1-6}$alkoxy, $R^iR^jN$—, $R^iR^jN$-carbonyl-, $R^iR^jN$—SO$_2$—, $R^iR^jN$-carbonyl-N(R$^a$)—;

$R^a$ and $R^b$ may be independently selected, for each occurrence, from the group consisting of: hydrogen and $C_{1-3}$alkyl; wherein $C_{1-3}$alkyl may optionally be substituted by one or more substituents selected from: fluorine, cyano, oxo and hydroxyl;

or $R^a$ and $R^b$, together with the nitrogen to which they are attached, may form a 4-6 membered heterocyclic ring which may have an additional heteroatom selected from O, S, or N; and wherein the 4-6 membered heterocyclic ring may optionally be substituted by one or more substituents selected from the group consisting of: fluorine, cyano, oxo or hydroxyl;

and pharmaceutically acceptable salts, stereoisomers, esters and prodrugs thereof.

In certain embodiments, $R^{A1}$ of the tricyclic compound of Formula II may be selected from the group consisting of hydrogen and fluorine.

Procedures for making compounds described herein are provided below with reference to Schemes 1-2. In the reactions described below, it may be necessary to protect reactive functional groups (such as hydroxyl, amino, thio or carboxyl groups) to avoid their unwanted participation in the reactions. The incorporation of such groups, and the methods required to introduce and remove them are known to those skilled in the art [for example, see Greene, Wuts, Protective Groups in Organic Synthesis. 2nd Ed. (1999)]. The deprotection step may be the final step in the synthesis such that the removal of protecting groups affords compounds of Formula I, as disclosed herein, or as exemplified in, for example, General Formula I, below. Starting materials used in the following schemes can be purchased or prepared by methods described in the chemical literature, or by adaptations thereof, using methods known by those skilled in the art. The order in which the steps are performed can vary depending on the groups introduced and the reagents used, but would be apparent to those skilled in the art.

The general synthetic strategy used to prepare the tricyclic compounds of General Formula I is depicted in Scheme 1. The tricyclic system may be assembled in a variety of ways, starting from an appropriately substituted and protected phenyl ring 1A. The group G' is a suitably protected carboxylic acid, such as a methyl- or tert-butyl carboxylate or is a functional group that may be readily converted into a carboxylic acid, such as a nitrile or aldehyde. The group G is a thioether, sulfoxide or sulfone, or a functional group that may be subsequently converted into a thioether, sulfoxide or sulfone group such as a halide or mesylate. The cyclopropane ring can be directly attached to the substituted phenyl ring to give intermediate 1B, and then the D'-ring can be formed by an intra-molecular reaction to give intermediate 1E. Alternatively, the cyclopropane ring can be attached to the substituted phenyl ring 1A via a linker, X', to give intermediate 1C, and then the D'-ring can be formed by an intra-molecular reaction to give intermediate 1E. Alternatively, the D'-ring can be built up onto the substituted phenyl ring to give intermediate 1 D, and then the cyclopropane ring formed to give intermediate 1E. Modifications to the cyclopropane and D' rings may be necessary to provide the required ring systems and this may be carried out prior to the formation of the tricyclic core or after it. For example, a dibromocyclopropane ring may be formed followed by removal of the bromines to give the unsubstituted cyclopropane ring.

Compounds of Formula I can be prepared from intermediate 1E by removal of any protecting groups. Alternatively, further modifications may be made to 1E, such as modifications at G, before the removal of any protecting groups to give compounds of General Formula I. Specific steps in the synthetic process are described in more detail below.

SCHEME 1

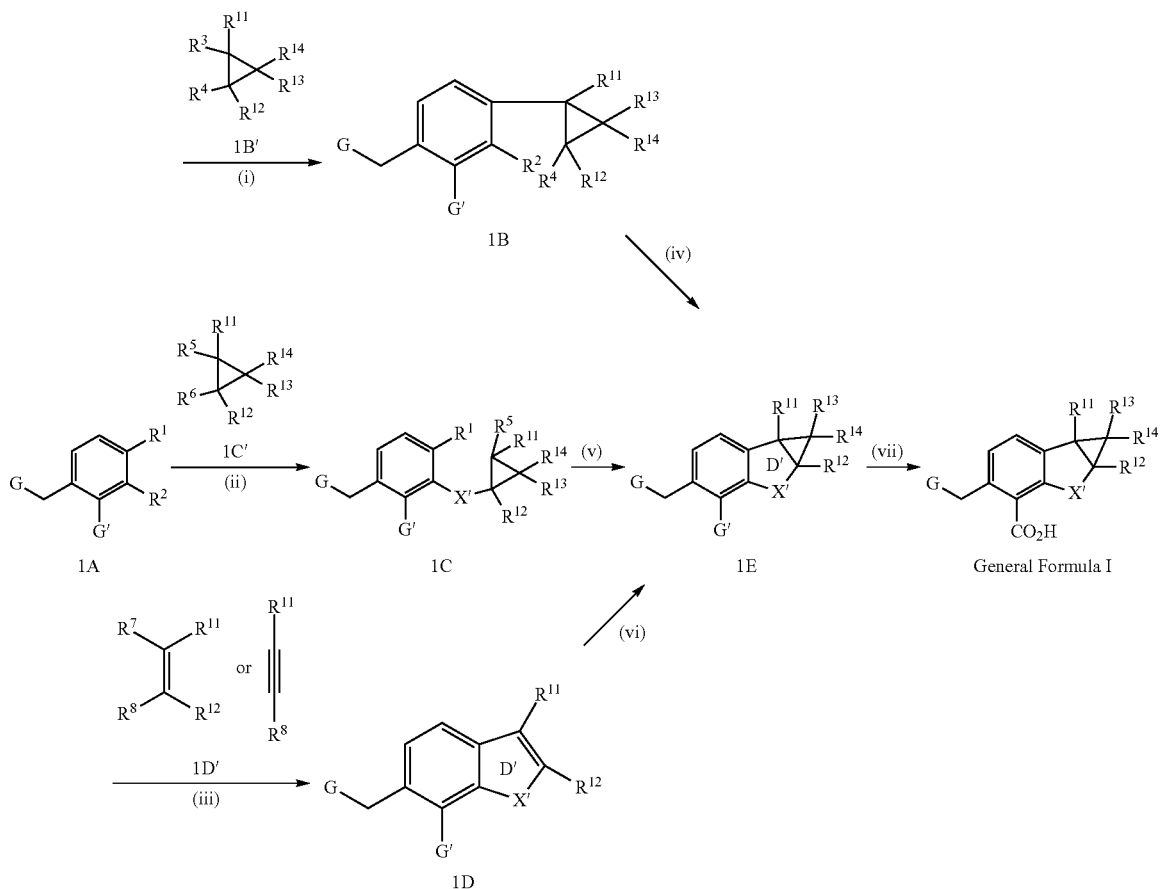

In Scheme 1, the carbon-carbon bond between the phenyl ring in 1A and the cyclopropane ring in 1B' in Step (i) may be formed under a range of coupling conditions to give compounds of structure 1B. The introduction of the cyclopropane ring may require a number of steps and the preparation of a number of intermediates. Protecting groups may also be required. If $R^1$ is a suitable leaving group (such as a halide or triflate), and $R^3$ is a borane, boronate or boronic acid group, then the carbon-carbon bond may be formed by treatment with a palladium catalyst (such as palladium chloride dppf or tris-(dibenzylideneacetone)-dipalladium, in the presence of a base (such as cesium carbonate) and a suitable reagent (such as a phosphine, for example tri-tert-butylphosphonium tetrafluoroborate) in an appropriate solvent (such as dioxane or water, or mixtures thereof), at a temperature between 50° C. and the reflux temperature of the solvent or alternatively by irradiating in the microwave at a temperature up to 180° C. A wide range of appropriate reagents and conditions are known to those skilled in the art to couple organoboranes, boronates and boronic acids to compounds such as 1A. [For example, see Miyaura, Suzuki, Chem. Rev. 1995, 95, 2457; Suzuki, Modern Arene Chemistry 2002, 53-106].

Alternatively, If $R^1$ is a suitable group (such as a halide or triflate), and $R^3$ is a trialkyl stannane (such as a tri-n-butyl stannane), then the carbon-carbon bond may be formed by treatment with a palladium catalyst (such as palladium chloride dppf), in an appropriate solvent (such as dimethoxyethane or tetrahydrofuran) at a temperature between 50° C. and the reflux temperature of the solvent or alternatively by irradiation in the microwave at a temperature up to 180° C. to give 1B. A wide range of appropriate reagents and conditions are known to those skilled in the art to couple stannanes to aryl halides such as 1A. [For example, see Smith, March, March's Advanced Organic Chemistry, 5$^{th}$ Edition, Wiley: New York, 2001, pp. 931-932; De Souza, Current Organic Synthesis 2006, 3(3), 313-326.].

Alternatively compounds of structure 1A, where $R^1$ is a suitable group (such as a halide or triflate), can be treated with, for example, a diboronate (such as bis-pinacolatodiboron) in the presence of a palladium catalyst (such as palladium chloride dppf) and a base (such as potassium acetate or diisopropylamine) in an appropriate solvent (such as a mixture of dioxane and water) at a temperature between 50° C. and the reflux temperature of the solvent or alternatively by irradiation in the microwave at a temperature up to 180° C. to give a compound of structure 1A, where $R^1$ is a boronate. A wide range of appropriate reagents and conditions are known to those skilled in the art to convert an aryl halide (or aryl triflate) to an arylboronate (or an arylborane) [for example, see Marshall, Chemtracts 2000, 13(4), 219-222]. The arylboronate (or arylborane) thus formed, can then be treated with compounds of structure 1B' (where $R^3$ is a halogen or triflate) in the presence of suitable reagents such as a phosphine (for example tri-tert-butyl-phosphonium tetrafluoroborate), a base (such as cesium carbonate) and a catalyst (such as tris-(dibenzylideneacetone)-dipalladium) in an appropriate solvent (such as a mixture of water and dioxane) at a temperature between 50° C. and the reflux temperature of the solvent or alternatively by irradiation in the microwave at a temperature up to 180° C. to afford compounds of structure 1B.

In Scheme 1, Step (iv), the groups $R^2$ and $R^4$ of compound 1B can be coupled together to give the group X', which forms the D'-ring. $R^2$ or $R^4$ may have been masked by protecting groups during Step (i), and may require deprotection before the group X' can be formed. Alternatively, $R^2$ or $R^4$ may require chemical modification before the group X' can be formed. For example if $R^2$ or $R^4$ is a nitro group, that group may be reduced, for example using hydrogen in the presence of a suitable catalyst (such as palladium on a solid support, such as carbon); or by treatment with an inorganic reducing agent (such as tin (II) chloride in DMF) to give an amino group. For example, if $R^2$ or $R^4$ is a hydroxyalkyl group, that group may be treated with an oxidising agent (such as Jones reagent or manganese dioxide) to give an aldehyde; or with a different oxidising agent (such as potassium permanganate) to give a carboxylic acid. For example, if $R^2$ or $R^4$ is an aldehyde, that group may be treated with an oxidising agent (such as potassium permanganate) to give a carboxylic acid or with a reducing agent (such as sodium borohydride) to give an alcohol. For example, if $R^2$ or $R^4$ is a ketone, that group may be treated with a reducing agent (such as sodium borohydride) to give a secondary alcohol. For example, if $R^2$ or $R^4$ is a carboxylic acid or ester, that group may be treated with a reducing agent (such as lithium aluminium hydride) to give an alcohol. For example, if $R^2$ or $R^4$ is an alkene group, that group may be treated with a borane (such as 9-borobicyclononane) and converted to a primary or secondary alcohol.

Formation of the linker X' may be carried out in a number of ways known to those skilled in the art. For example, if the group $R^2$ is a hydroxyl and the group $R^4$ is a substituted alkylalcohol then 1B can be treated with a dehydrating agent (such as diisopropyl azodicarboxylate) in the presence of a phosphine, (such as triphenylphosphine) to give 1E, where X' is an ether. Alternatively, if one of the two groups $R^2$ or $R^4$ is a hydroxyl and the other group is an alkyl group substituted with a leaving group (such as a halogen, tosylate or triflate) 1B can be treated with a base (such as diisopropylethylamine, potassium carbonate or sodium hydride) to form 1E, where X' is an ether.

Alternatively, if the group $R^4$ is a carboxylic acid and $R^2$ is an alkyl halide or sulfonate, then 1B can be treated with a base such as diisopropyl-ethylamine, potassium carbonate or sodium hydride to form 1E, where X' is an ester.

Alternatively, if the group $R^2$ is a hydroxyl, or substituted alkylalcohol and $R^4$ is a carboxylic acid or ester or an alkyl group substituted by a carboxylic acid or ester, then 1B can be treated with an acid (such as hydrochloric acid) or dehydrating agent (such as dicyclohexylcarbodiimide or acetic anhydride) to form 1E, where X' is an ester.

Alternatively, if the group $R^2$ on 1B is a hydroxyl or substituted alkylalcohol and $R^4$ is a carboxylic acid or an alkyl group substituted by a carboxylic acid, then the carboxylic acid can first be converted to a mixed anhydride (for example by treatment with 2,4,6-trichlorobenzoyl chloride) or to an activated ester (for example by treatment with HATU in the presence of a base such as diisopropylethylamine or pyridine), and the resulting mixed anhydride or activated ester can be further treated with a base (such as diisopropylethylamine, pyridine or potassium carbonate) to form 1E, where X' is an ester.

Alternatively, if the group $R^2$ on 1B is an amine or a substituted alkylamine and the group $R^4$ is a carboxylic acid or an alkyl group substituted by a carboxylic acid, the carboxylic acid can be converted to an activated ester (for example by treatment with HATU and a base such as diisopropylethylamine or pyridine or TBTU in the presence of N-methylmorpholine), and the resulting activated ester can be further treated with a base to form 1E where X' is an amide.

Alternatively, if the group $R^2$ on 1B is an amine, or a substituted alkylamine and the group $R^4$ is a carboxylic acid or an alkyl group substituted by a carboxylic acid, then 1B can then be treated with a dehydrating agent (such as such as diisopropylcarbodiimide) to form 1E, where X' is an amide.

Alternatively, if one of the two groups $R^2$ or $R^4$ is an amine, or substituted alkylamine and the other group is an alkyl group substituted with a leaving group (such as a halogen, tosylate or triflate) then 1B can be treated with a base (such as diisopropylethylamine, pyridine or potassium carbonate) to form 1E, where X' is a substituted amine.

In Scheme 1, Step (ii), compounds of the structure 1A can be reacted with 1C' to form the linker X' and give compounds of the structure 1C. The formation of the linker X' in compounds with the structure 1C may require a number of steps and the preparation of a number of intermediates, and the use of protecting groups may also be required. The linker X' may be prepared using one of the methods described for Step (iv) in the formation of 1E.

In Scheme 1, Step (v), compounds of structure 1E may be prepared from compounds of structure 1C by reaction of the groups $R^1$ and $R^5$ under a range of conditions to form a carbon-carbon bond. The carbon-carbon bond may be formed using one of the methods described for Step (i) in the formation of 1B.

In Scheme 1, Step (iii), compounds of structure 1A may be reacted under a range of conditions with intermediates of the type 1D' to give compounds of structure 1D where D' is a six- or seven-membered fused carbocyclic or heterocyclic ring. The groups $R^1$ and $R^7$ may be reacted together to form a carbon-carbon bond, and the groups $R^2$ and $R^8$ may be reacted together to form the group X'. Methods to form bicyclic compounds of structure 1D from substituted phenyl rings of structure 1A are well known to those skilled in the art (see Comprehensive Heterocyclic Chemistry Ed.: Katritzky, Ramsden, Scriven, and Taylor, Elsevier, 2008).

For example, a compound of structure 1A, where $R^2$ is a hydroxyl and $R^1$ is hydrogen, can be treated with a propargyl halide or tosylate or a substituted propargyl halide or tosylate in the presence of a base (such as potassium carbonate or cesium carbonate) in a solvent (such as acetone) at a temperature between room temperature and the reflux temperature of the solvent to give a compound of type 1A in which $R^2$ is a propargyloxyl or substituted propargyloxy group. This intermediate may be heated to ~200° C. or treated with an appropriate catalyst, such as a gold catalyst, for example triphenylphosphine gold triflamide) in an appropriate solvent (such as toluene) at a temperature between 80° C. and the reflux temperature of the solvent to give a compound of structure 1D wherein X' is —OCH$_2$—.

In Scheme 1, Step (vi), compounds of structure 1D, may be treated with diethyl zinc and di-iodomethane optionally in the presence of additional reagents (such as trifluoroacetic acid or zinc iodide) in a solvent (such as 1,2-dichloroethane) at a temperature between −78° C. and room temperature to give compounds of structure 1E. Alternatively, compounds of structure 1D, may be treated with trimethyl sulfoxonium iodide or trimethyl sulphonium iodide in the presence of a base (such as sodium hydride) in a solvent (such as dimethyl sulfoxide) at a temperature between room temperature and 100° C. Alternatively, compounds of structure 1D, may be treated with diazomethane in the presence of a catalyst (such as palladium acetate) in a solvent such as diethyl ether at a temperature between 0° C. and room temperature.

Alternatively, compounds of structure 1E may be prepared from compounds of structure 1D in a two step procedure. For example, compounds of structure 1D, may be treated with trimethylsilyl diazomethane in the presence of a catalyst (such as palladium acetate) in a solvent (such as diethyl ether) at a temperature between 0° C. and room temperature to give an intermediate of structure 1E in which $R^{13}$ is H and $R^{14}$ is a trimethyl silyl group. This intermediate may be converted to compounds of structure 1E in which $R^{13}$ and $R^{14}$ are both H, by treatment with a source of fluoride, (for example tetrabutyl ammonium fluoride) in a solvent (such as tetrahydrofuran) at a temperature between 0° C. and room temperature.

Alternatively, compounds of structure 1D may be treated with a haloform (such as chloroform or bromoform) in the presence of a base such as sodium hydroxide or potassium t-butoxide in the presence of a catalyst (such as triethylbenzylammonium chloride or tetrabutyl ammonium bromide) in a mixture of water and a halogenated solvent (such as dichloromethane or dichloroethane) or alternatively in excess of the haloform, at a temperature between room temperature and 80° C. to give an intermediate compound of structure 1E in which $R^{13}$ and $R^{14}$ are both chlorine or bromine. This intermediate may be converted to compounds of structure 1E in which $R^{13}$ and $R^{14}$ are both H by treatment with a base (such as sodium methoxide or sodium t-butoxide) in a solvent (such as tetrahydrofuran) at a temperature between room temperature and the reflux temperature of the solvent. Alternatively, the intermediate of structure 1E in which $R^{13}$ and $R^{14}$ are both chlorine or bromine may be converted to compounds of structure 1E in which $R^{13}$ and $R^{14}$ are both H by reduction; for example, by treatment with lithium aluminium hydride in a solvent (such as tetrahydrofuran) at a temperature between 0° C. and the reflux temperature of the solvent or alternatively, for example by hydrogenation using a catalyst (such as palladium on carbon) in a solvent (such as methanol or ethanol), optionally in the presence of a base (such as triethylamine) or alternatively by treatment with a metal reducing agent such as zinc, in the presence of a catalyst such as ammonium chloride. Alternatively, the intermediate of structure 1E in which $R^{13}$ and $R^{14}$ are both chlorine or bromine may be converted to compounds of structure 1E, in which $R^{13}$ and $R^{14}$ are both H, under radical conditions; for example, by treatment with a tin hydride (such as tributyl tin hydride) optionally in the presence of a radical initiator (such as azo-bis-isobutyronitrile) in a solvent (such as toluene) at a temperature between room temperature and the reflux temperature of the solvent.

Alternatively, compounds of structure 1E, in which $R^{13}$ and $R^{14}$ are both fluorine may be prepared by the treatment of compounds of structure 1D by treatment with a source of difluorocarbene. For example, by treatment with sodium difluorochloroacetate or difluorobromoacetate in an ether solvent such as diethyleneglycol dimethyl ether while heating at a temperature between 130° C. and 180° C.

In Scheme 1, Step (vii), compounds of general structure 1E may be converted to compounds of General Formula I by the conversion of the group G' to a carboxylic acid. If the group G' is a carboxylic ester (such as a methyl, tert-butyl or benzyl ester) then a variety of reagents and conditions can be used to convert 1E into a compound of the General Formula I. For example, if G' is a methyl, ethyl or benzyl ester, it may be converted to a carboxylic acid by treatment with an inorganic base (such as lithium hydroxide or sodium hydroxide) in a solvent (such as methanol, dioxane or water, or mixtures thereof) at a temperature between room temperature and the reflux temperature of the solvent, or alternatively by microwave irradiation at 120-180° C. for 10 minutes to 1 hour. Alternatively if G' is a benzyl ester it may be converted to a carboxylic acid by hydrogenation in the presence of a catalyst (such as palladium on a solid support such as carbon) in a solvent (such as dioxane or ethyl acetate).

Alternatively if G' is a tert-butyl ester, it may be converted to a carboxylic acid by treatment with an acid (such as trifluoroacetic acid or hydrogen chloride) in a solvent (such as dichloromethane or dioxane).

Alternatively, if the group G' is a nitrile, it may be converted into a carboxylic acid by treatment with aqueous acid (such as a mineral acid, for example hydrochloric acid) under appropriate conditions (such as heating, for example to reflux); or by treatment with aqueous base (such as an aqueous hydroxide, for example aqueous sodium hydroxide) under appropriate conditions (such as heating, for example to reflux).

Alternatively, if the group G' is an aldehyde or a hydroxymethyl moiety then it may be converted into a carboxylic acid by treatment with a suitable oxidising reagent (such as potassium permanganate or chromic acid).

The general synthetic strategy to modify the group G is depicted in Scheme 2. The G group may be introduced and/or modified either before, during or after the assembly of the tricyclic ring system. It may be that the group G is protected during the sequence to form the tricyclic ring system and these protecting groups will need to be removed or modified prior to conversion to the sulfone moiety. For example, the group G may be a methoxy group during the earlier sequence. Conversion of this methoxy group to an appropriate leaving group such as a halogen may be achieved by treatment with acetyl chloride in the presence of, for example, zinc chloride in a solvent (such as diethyl ether) at a temperature between room temperature and the reflux temperature of the solvent. Specific steps used to assemble sulfone are described in more detail below.

oxidation may be carried out by treatment of compounds of structure 2B with hydrogen peroxide in a solvent (such as acetic acid) at a temperature between room temperature and the reflux temperature of the solvent. Alternative oxidizing agents may be used to convert compounds of structure 2B to compounds of structure 2C such a 3-chloroperbenzoic acid in a chlorinated solvent (such as dichloromethane) at a temperature between 0° C. and the reflux temperature of the solvent. A wide range of reagents and conditions are known to one skilled in the art for the oxidation of thiols to sulfones. [for example, see Drabowicz, Kielbasinski, Mikolajczyk in Patai, Rappoport, Stirling *The Chemistry of Sulphones and Sulphoxides*; Wiley: New York, 1988, pp. 233-378, pp 235-255. Madesclaire *Tetrahedron* 1986, 42, 549-5495. Oae *The Organic Chemistry of Sulfur*; Plenum: New York 1977, pp. 385-390. Smith, March, *March's Advanced Organic Chemistry*, 5$^{th}$ Edition, Wiley: New York, 2001, pp. 1541-1542].

Alternatively in Scheme 2, Step (iii), compounds of structure 2A may be converted directly to compounds of structure 2C by treatment with an appropriately substituted sulfinate in the presence of a base (such as sodium bicarbonate, potassium bicarbonate or di-isopropylethylamine) in a solvent (such as a mixture of dimethyl acetamide and water) at a temperature between room temperature and the reflux temperature of the solvent.

Compounds of any of Formula I or, for example, General Formula I as depicted above, or any of the intermediates described in the schemes above, can be further derivatised by using one or more standard synthetic methods known to those skilled in the art. Such methods can involve substitution, oxidation or reduction reactions. These methods can also be used to obtain or modify compounds of General Formula I or any preceding intermediates by modifying,

SCHEME 2

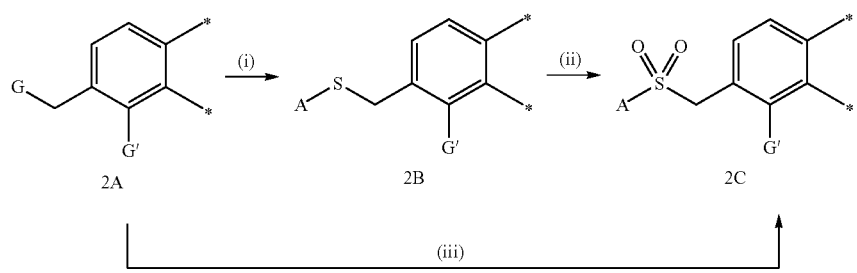

In Scheme 2, the asterisks denote either the presence of the groups R$^1$ and R$^2$ (as shown in Scheme 1) or the presence of the tricyclic ring system, or intermediates towards the ring system (as shown in Scheme 1).

In Scheme 2, Step (i), if G is a suitable leaving group, such as a halide (chloride or bromide) or triflate, it may be reacted with an appropriately substituted thiol in the presence of a base (such as potassium carbonate) in a solvent (such as acetone or THF) at a temperature between room temperature and the reflux temperature of the solvent. A wide range of reagents and conditions are known to one skilled in the art for the conversion of compounds of structure 2A in which G is a leaving group to compounds of structure 2B [for example, see Peach in Patai *The Chemistry of the Thiol Group, pt* 2; Wiley: New York, 1974, pp. 721].

In Scheme 2, Step (ii) compounds of structure 2B may be converted to compounds of structure 2C by oxidation. The introducing or removing appropriate functional groups. Particular substitution approaches include alkylation, arylation, heteroarylation, acylation, thioacylation, halogenation, sulfonylation, nitration, formylation, hydrolysis and coupling procedures. These procedures can be used to introduce a functional group onto the parent molecule (such as the nitration or sulfonylation of aromatic rings) or to couple two molecules together (for example to couple an amine to a carboxylic acid to afford an amide; or to form a carbon-carbon bond between two heterocycles). For example, alcohol or phenol groups can be converted to ether groups by coupling a phenol with an alcohol in a solvent (such as tetrahydrofuran) in the presence of a phosphine (such as triphenylphosphine) and a dehydrating agent (such as diethyl, diisopropyl or dimethyl azodicarboxylate). Alternatively, ether groups can be prepared by deprotonation of an alcohol, using a suitable base (such as sodium hydride)

followed by the addition of an alkylating agent (such as an alkyl halide or an alkyl sulfonate).

In another example, a primary or secondary amine can be alkylated using a reductive alkylation procedure. For example, the amine can be treated with an aldehyde and a borohydride (such as sodium triacetoxyborohydride, or sodium cyanoborohydride) in a solvent (such as a halogenated hydrocarbon, for example dichloromethane, or an alcohol, for example ethanol) and, where necessary, in the presence of an acid (such as acetic acid).

In another example, hydroxy groups (including phenolic OH groups) can be converted into leaving groups, such as halogen atoms or sulfonyloxy groups (such as alkylsulfonyloxy, for example trifluoromethanesulfonyloxy, or aryl suphonyloxy, for example p-toluenesulfonyloxy) using conditions known to those skilled in the art. For example, an aliphatic alcohol can be reacted with thionyl chloride in a halogenated hydrocarbon (such as dichloromethane) to afford the corresponding alkyl chloride. A base (such as triethylamine) can also be used in the reaction.

In another example, ester groups can be converted to the corresponding carboxylic acid by acid- or base-catalysed hydrolysis depending on the nature of the ester group. Acid catalysed hydrolysis can be achieved by treatment with an organic or inorganic acid (such as trifluoroacetic acid in an aqueous solvent, or a mineral acid such as hydrochloric acid in a solvent such as dioxane). Base catalysed hydrolysis can be achieved by treatment with an alkali metal hydroxide (such as lithium hydroxide in an aqueous alcohol, for example methanol).

In another example, aromatic halogen substituents in the compounds may be subjected to halogen-metal exchange by treatment with a base (such as a lithium base, for example n-butyl or t-butyl lithium) optionally at a low temperature (such as −78° C.) in a solvent (such as tetrahydrofuran) and the mixture may then be quenched with an electrophile to introduce a desired substituent. Thus, for example, a formyl group can be introduced by using dimethylformamide as the electrophile. Aromatic halogen substituents can also be subjected to palladium catalysed reactions to introduce groups such as carboxylic acids, esters, cyano or amino substituents.

In another example, an aryl, or heteroaryl ring substituted with an appropriate leaving group (such as a halogen or sulfonyl ester, for example a triflate) can undergo a palladium catalysed coupling reaction with a wide variety of substrates to form a carbon-carbon bond. For example, a Heck reaction can be used to couple such a ring system to an alkene (which may, or may not, be further substituted) by treatment with an organopalladium complex (such as tetrakis(triphenylphosphine)palladium(0), palladium (II) acetate or palladium (II) chloride) in the presence of a ligand (such as a phosphine, for example triphenylphosphine) in the presence of a base (such as potassium carbonate or a tertiary amine, for example, triethylamine), in an appropriate solvent (such as tetrahydrofuran or DMF), under appropriate conditions (such as heating to, for example, 50-120° C.). In another example, a Sonogashira reaction can be used to couple such a ring system to an alkyne (which may, or may not be further substituted) by treatment with a palladium complex (such as tetrakis(triphenylphosphine)palladium(0)) and a halide salt of copper (I) (such as copper (I) iodide), in the presence of a base (such as a potassium carbonate or a tertiary amine, for example, triethylamine), in an appropriate solvent (such as tetrahydrofuran or dimethylformamide), under appropriate conditions (such as heating to, for example, 50-120° C.). In another example, a Stille reaction can be used to couple such a ring system to an alkene, by treatment with an organotin compound (such as an alkynyltin or alkenyltin reagent, for example an alkenyltributylstannane) in the presence of a palladium complex (such as tetrakis(triphenylphosphine)palladium(0)), with, or without the presence of a salt (such as a copper (1) halide), in an appropriate solvent (such as dioxane or dimethylformamide), under appropriate conditions (such as heating to, for example, 50-120° C.).

Particular oxidation approaches include dehydrogenations and aromatisation, decarboxylation and the addition of oxygen to certain functional groups. For example, aldehyde groups can be prepared by oxidation of the corresponding alcohol using conditions well known to those skilled in the art. For example, an alcohol can be treated with an oxidising agent (such as Dess-Martin periodinane) in a solvent (such as a halogenated hydrocarbon, for example dichloromethane). Alternative oxidising conditions can be used, such as treatment with oxalyl chloride and an activating amount of dimethylsulfoxide and subsequent quenching by the addition of an amine (such as triethylamine). Such a reaction can be carried out in an appropriate solvent (such as a halogenated hydrocarbon, for example dichloromethane) and under appropriate conditions (such as cooling below room temperature, for example to −78° C. followed by warming to room temperature). In another example, sulfur atoms can be oxidised to the corresponding sulfoxide or sulfone using an oxidising agent (such as a peroxy acid, for example 3-chloroperoxybenzoic acid) in an inert solvent (such as a halogenated hydrocarbon, for example dichloromethane) at around ambient temperature.

Particular reduction approaches include the removal of oxygen atoms from particular functional groups or saturation (or partial saturation) of unsaturated compounds including aromatic or heteroaromatic rings. For example, primary alcohols can be generated from the corresponding ester or aldehyde by reduction, using a metal hydride (such as lithium aluminium hydride or sodium borohydride in a solvent such as methanol). Alternatively, $CH_2OH$ groups can be generated from the corresponding carboxylic acid by reduction, using a metal hydride (such as lithium aluminium hydride in a solvent such as tetrahydrofuran). In another example, a nitro group may be reduced to an amine by catalytic hydrogenation in the presence of a metal catalyst (such as palladium on a solid support such as carbon) in a solvent (such as an ether, for example tetrahydrofuran, or an alcohol, such as methanol), or by chemical reduction using a metal (such as zinc, tin or iron) in the presence of an acid (such as acetic acid or hydrochloric acid). In a further example an amine can be obtained by reduction of a nitrile, for example by catalytic hydrogenation in the presence of a metal catalyst (such as palladium on a solid support such as carbon), or Raney nickel in a solvent (such as tetrahydrofuran) and under suitable conditions (such as cooling to below room temperature, for example to −78° C., or heating, for example to reflux).

Salts of compounds of General Formula I can be prepared by the reaction of a compound of General Formula I with an appropriate acid or base in a suitable solvent, or mixture of solvents (such as an ether, for example, diethyl ether, or an alcohol, for example ethanol, or an aqueous solvent) using conventional procedures. Salts of compound of General Formula I can be exchanged for other salts by treatment using conventional ion-exchange chromatography procedures.

Where it is desired to obtain a particular enantiomer of a compound of General Formula I, this may be produced from a corresponding mixture of enantiomers by employing any suitable conventional procedure for resolving enantiomers. For example, diastereomeric derivatives (such as salts) can be produced by reaction of a mixture of enantiomers of a compound of General Formula I (such as a racemate) and an appropriate chiral compound (such as a chiral base). The diastereomers can then be separated by any conventional means such as crystallisation, and the desired enantiomer recovered (such as by treatment with an acid in the instance where the diastereomer is a salt). Alternatively, a racemic mixture of esters can be resolved by kinetic hydrolysis using a variety of biocatalysts (for example, see Patel Steroselective Biocatalysts, Marcel Decker; New York 2000).

In another resolution process a racemate of compounds of General Formula I can be separated using chiral High Performance Liquid Chromatography. Alternatively, a particular enantiomer can be obtained by using an appropriate chiral intermediate in one of the processes described above. Chromatography, recrystallisation and other conventional separation procedures may also be used with intermediates or final products where it is desired to obtain a particular geometric isomer of the invention.

II. Methods

Another aspect of the invention provides methods of modulating the activity of MetAP2. Such methods comprise exposing said receptor to a compound described herein. In some embodiments, the compound utilized by one or more of the foregoing methods is one of the generic, subgeneric, or specific compounds described herein, such as a compound of Formula I, Ia, Ib, Ic, Id, or II. The ability of compounds described herein to modulate or inhibit MetAP2 can be evaluated by procedures known in the art and/or described herein. Another aspect of the invention provides methods of treating a disease associated with expression or activity of MetAP2 in a patient. For example, a contemplated method includes administering a disclosed compound in an amount sufficient to establish inhibition of intracellular MetAP2 effective to increase thioredoxin production in the patient and to induce multi organ stimulation of anti-obesity processes in the subject, for example, by administering a disclosed compound in an amount insufficient to reduce angiogenesis in the patient.

In certain embodiments, the invention provides a method of treating and or ameliorating obesity in a patient by administering an effective amount of a disclosed compound. Also provided herein are methods for inducing weight loss in a patient in need thereof. Contemplated patients include not only humans, but other animals such as companion animals (e.g., dogs, cats).

Other contemplated methods of treatment include method of treating or ameliorating an obesity-related condition or co-morbidity, by administering a compound disclosed herein to a subject. For example, contemplated herein are methods for treating type 2 diabetes in a patient in need thereof.

Exemplary co-morbidities include cardiac disorders, endocrine disorders, respiratory disorders, hepatic disorders, skeletal disorders, psychiatric disorders, metabolic disorders, and reproductive disorders.

Exemplary cardiac disorders include hypertension, dyslipidemia, ischemic heart disease, cardiomyopathy, cardiac infarction, stroke, venous thromboembolic disease and pulmonary hypertension. Exemplary endocrine disorders include type 2 diabetes and latent autoimmune diabetes in adults. Exemplary respiratory disorders include obesity-hypoventilation syndrome, asthma, and obstructive sleep apnea. An exemplary hepatic disorder is nonalcoholic fatty liver disease. Exemplary skeletal disorders include back pain and osteoarthritis of weight-bearing joints. Exemplary metabolic disorders include Prader-Willi Syndrome and polycystic ovary syndrome. Exemplary reproductive disorders include sexual dysfunction, erectile dysfunction, infertility, obstetric complications, and fetal abnormalities. Exemplary psychiatric disorders include weight-associated depression and anxiety.

In particular, in certain embodiments, the invention provides a method of treating the above medical indications comprising administering to a subject in need thereof a therapeutically effective amount of a compound described herein, such as a compound of Formula I, Ia, Ib, Ic, Id, or II.

Obesity or reference to "overweight" refers to an excess of fat in proportion to lean body mass. Excess fat accumulation is associated with increase in size (hypertrophy) as well as number (hyperplasia) of adipose tissue cells. Obesity is variously measured in terms of absolute weight, weight:height ratio, distribution of subcutaneous fat, and societal and esthetic norms. A common measure of body fat is Body Mass Index (BMI). The BMI refers to the ratio of body weight (expressed in kilograms) to the square of height (expressed in meters). Body mass index may be accurately calculated using either of the formulas: weight(kg)/height$^2$ (m$^2$) (SI) or 703× weight(lb)/height$^2$(in$^2$) (US).

In accordance with the U.S. Centers for Disease Control and Prevention (CDC), an overweight adult has a BMI of 25 kg/m$^2$ to 29.9 kg/m$^2$, and an obese adult has a BMI of 30 kg/m$^2$ or greater. A BMI of 40 kg/m$^2$ or greater is indicative of morbid obesity or extreme obesity. Obesity can also refer to patients with a waist circumference of about 102 cm for males and about 88 cm for females. For children, the definitions of overweight and obese take into account age and gender effects on body fat. Patients with differing genetic background may be considered "obese" at a level differing from the general guidelines, above.

The compounds of the present invention also are useful for reducing the risk of secondary outcomes of obesity, such as reducing the risk of left ventricular hypertrophy. Methods for treating patients at risk of obesity, such as those patients who are overweight, but not obese, e.g. with a BMI of between about 25 and 30 kg/m$^2$, are also contemplated. In certain embodiments, a patient is a human.

BMI does not account for the fact that excess adipose can occur selectively in different parts of the body, and development of adipose tissue can be more dangerous to health in some parts of the body rather than in other parts of the body. For example, "central obesity", typically associated with an "apple-shaped" body, results from excess adiposity especially in the abdominal region, including belly fat and visceral fat, and carries higher risk of co-morbidity than "peripheral obesity", which is typically associated with a "pear-shaped" body resulting from excess adiposity especially on the hips. Measurement of waist/hip circumference ratio (WHR) can be used as an indicator of central obesity. A minimum WHR indicative of central obesity has been variously set, and a centrally obese adult typically has a WHR of about 0.85 or greater if female and about 0.9 or greater if male.

Methods of determining whether a subject is overweight or obese that account for the ratio of excess adipose tissue to lean body mass involve obtaining a body composition of the subject. Body composition can be obtained by measuring the thickness of subcutaneous fat in multiple places on the body, such as the abdominal area, the subscapular region, arms, buttocks and thighs. These measurements are then used to estimate total body fat with a margin of error of approximately four percentage points. Another method is bioelectrical impedance analysis (BIA), which uses the resistance of electrical flow through the body to estimate body fat. Another method is using a large tank of water to measure body buoyancy. Increased body fat will result in greater buoyancy, while greater muscle mass will result in a tendency to sink.

In another aspect, the invention provides methods for treating an overweight or obese subject involving determining a level of at least one biomarker related to being overweight or obese in the subject, and administering an effective amount of a disclosed compound to achieve a target level in the subject. Exemplary biomarkers include body weight, Body Mass Index (BMI), Waist/Hip ratio WHR, plasma adipokines, and a combination of two or more thereof.

In certain embodiments, the compound utilized by one or more of the foregoing methods is one of the generic, subgeneric, or specific compounds described herein, such as a compound of Formula I, Ia, Ib, Ic, Id, or II.

The compounds of the invention may be administered to patients (animals and humans) in need of such treatment in dosages that will provide optimal pharmaceutical efficacy. It will be appreciated that the dose required for use in any particular application will vary from patient to patient, not only with the particular compound or composition selected, but also with the route of administration, the nature of the condition being treated, the age and condition of the patient, concurrent medication or special diets then being followed by the patient, and other factors which those skilled in the art will recognize, with the appropriate dosage ultimately being at the discretion of the attendant physician. For treating clinical conditions and diseases noted above, a compound of this invention may be administered orally, subcutaneously, topically, parenterally, by inhalation spray or rectally in dosage unit formulations containing conventional non-toxic pharmaceutically acceptable carriers, adjuvants and vehicles. Parenteral administration may include subcutaneous injections, intravenous or intramuscular injections or infusion techniques.

Treatment can be continued for as long or as short a period as desired. The compositions may be administered on a regimen of, for example, one to four or more times per day. A suitable treatment period can be, for example, at least about one week, at least about two weeks, at least about one month, at least about six months, at least about 1 year, or indefinitely. A treatment period can terminate when a desired result, for example a weight loss target, is achieved. A treatment regimen can include a corrective phase, during which dose sufficient to provide reduction of weight is administered, and can be followed by a maintenance phase, during which a e.g. a lower dose sufficient to prevent weight gain is administered. A suitable maintenance dose is likely to be found in the lower parts of the dose ranges provided herein, but corrective and maintenance doses can readily be established for individual subjects by those of skill in the art without undue experimentation, based on the disclosure herein. Maintenance doses can be employed to maintain body weight in subjects whose body weight has been previously controlled by other means, including diet and exercise, bariatric procedures such as bypass or banding surgeries, or treatments employing other pharmacological agents.

III. Pharmaceutical Compositions and Kits

Another aspect of the invention provides pharmaceutical compositions comprising compounds as disclosed herein formulated together with a pharmaceutically acceptable carrier. In particular, the present disclosure provides pharmaceutical compositions comprising compounds as disclosed herein formulated together with one or more pharmaceutically acceptable carriers. These formulations include those suitable for oral, rectal, topical, buccal, parenteral (e.g., subcutaneous, intramuscular, intradermal, or intravenous) rectal, vaginal, or aerosol administration, although the most suitable form of administration in any given case will depend on the degree and severity of the condition being treated and on the nature of the particular compound being used. For example, disclosed compositions may be formulated as a unit dose, and/or may be formulated for oral or subcutaneous administration.

Exemplary pharmaceutical compositions of this invention may be used in the form of a pharmaceutical preparation, for example, in solid, semisolid or liquid form, which contains one or more of the compound of the invention, as an active ingredient, in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The active object compound is included in the pharmaceutical composition in an amount sufficient to produce the desired effect upon the process or condition of the disease.

For preparing solid compositions such as tablets, the principal active ingredient may be mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules.

In solid dosage forms for oral administration (capsules, tablets, pills, dragees, powders, granules and the like), the subject composition is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the subject composition moistened with an inert liquid diluent. Tablets, and other solid dosage forms, such as dragees, capsules, pills and granules, may optionally be scored or prepared with coatings and shells, such as enteric coatings and other coatings well known in the pharmaceutical-formulating art.

Compositions for inhalation or insufflation include solutions and suspensions in pharmaceutically acceptable, aqueous or organic solvents, or mixtures thereof, and powders. Liquid dosage forms for oral administration include pharmaceutically acceptable emulsions, microemulsions, solutions, suspensions, syrups and elixirs. In addition to the subject composition, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, cyclodextrins and mixtures thereof.

Suspensions, in addition to the subject composition, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing a subject composition with one or more suitable non-irritating excipients or carriers comprising, for example, cocoa butter, polyethylene glycol, a suppository wax or a salicylate, and which is solid at room temperature, but liquid at body temperature and, therefore, will melt in the body cavity and release the active agent.

Dosage forms for transdermal administration of a subject composition include powders, sprays, ointments, pastes, creams, lotions, gels, solutions, patches and inhalants. The active component may be mixed under sterile conditions with a pharmaceutically acceptable carrier, and with any preservatives, buffers, or propellants which may be required.

The ointments, pastes, creams and gels may contain, in addition to a subject composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays may contain, in addition to a subject composition, excipients such as lactose, talc, silicic acid, aluminum hydroxide, calcium silicates and polyamide powder, or mixtures of these substances. Sprays may additionally contain customary propellants, such as chlorofluorohydrocarbons and volatile unsubstituted hydrocarbons, such as butane and propane.

Compositions and compounds of the present invention may alternatively be administered by aerosol. This is accomplished by preparing an aqueous aerosol, liposomal preparation or solid particles containing the compound. A non-aqueous (e.g., fluorocarbon propellant) suspension could be used. Sonic nebulizers may be used because they minimize exposing the agent to shear, which may result in degradation of the compounds contained in the subject compositions.

Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include non-ionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Pharmaceutical compositions of this invention suitable for parenteral administration comprise a subject composition in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate and cyclodextrins. Proper fluidity may be maintained, for example, by the use of coating materials, such as lecithin, by the maintenance of the required particle size in the case of dispersions, and by the use of surfactants In another aspect, the invention provides enteral pharmaceutical formulations including a disclosed compound and an enteric material; and a pharmaceutically acceptable carrier or excipient thereof. Enteric materials refer to polymers that are substantially insoluble in the acidic environment of the stomach, and that are predominantly soluble in intestinal fluids at specific pHs. The small intestine is the part of the gastrointestinal tract (gut) between the stomach and the large intestine, and includes the duodenum, jejunum, and ileum. The pH of the duodenum is about 5.5, the pH of the jejunum is about 6.5 and the pH of the distal ileum is about 7.5. Accordingly, enteric materials are not soluble, for example, until a pH of about 5.0, of about 5.2, of about 5.4, of about 5.6, of about 5.8, of about 6.0, of about 6.2, of about 6.4, of about 6.6, of about 6.8, of about 7.0, of about 7.2, of about 7.4, of about 7.6, of about 7.8, of about 8.0, of about 8.2, of about 8.4, of about 8.6, of about 8.8, of about 9.0, of about 9.2, of about 9.4, of about 9.6, of about 9.8, or of about 10.0. Exemplary enteric materials include cellulose acetate phthalate (CAP), hydroxypropyl methylcellulose phthalate (HPMCP), polyvinyl acetate phthalate (PVAP), hydroxypropyl methylcellulose acetate succinate (HPMCAS), cellulose acetate trimellitate, hydroxypropyl methylcellulose succinate, cellulose acetate succinate, cellulose acetate hexahydrophthalate, cellulose propionate phthalate, cellulose acetate maleate, cellulose acetate butyrate, cellulose acetate propionate, copolymer of methylmethacrylic acid and methyl methacrylate, copolymer of methyl acrylate, methylmethacrylate and methacrylic acid, copolymer of methylvinyl ether and maleic anhydride (Gantrez ES series), ethyl methyacrylate-methylmethacrylate-chlorotrimethylammonium ethyl acrylate copolymer, natural resins such as zein, shellac and copal collophorium, and several commercially available enteric dispersion systems (e.g., Eudragit L30D55, Eudragit FS30D, Eudragit L100, Eudragit S 100, Kollicoat EMM30D, Estacryl 30D, Coateric, and Aquateric). The solubility of each of the above materials is either known or is readily determinable in vitro. The foregoing is a list of possible materials, but one of skill in the art with the benefit of the disclosure would recognize that it is not comprehensive and that there are other enteric materials that would meet the objectives of the present invention.

Advantageously, the invention also provides kits for use by a e.g. a consumer in need of weight loss. Such kits include a suitable dosage form such as those described above and instructions describing the method of using such dosage form to mediate, reduce or prevent inflammation. The instructions would direct the consumer or medical personnel to administer the dosage form according to administration modes known to those skilled in the art. Such kits could advantageously be packaged and sold in single or multiple kit units. An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are scaled in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc. . . . Second Week, Monday, Tuesday, . . . " etc. Other variations of memory aids will be readily apparent. A "daily dose" can be a single tablet or capsule or several pills or capsules to be taken on a given day. Also, a daily dose of a first compound can consist of one tablet or capsule while a daily dose of the second compound can consist of several tablets or capsules and vice versa. The memory aid should reflect this.

Also contemplated herein are methods and compositions that include a second active agent, or administering a second active agent. For example, in addition to being overweight or obese, a subject or patient can further have overweight- or obesity-related co-morbidities, i.e., diseases and other adverse health conditions associated with, exacerbated by, or precipitated by being overweight or obese. Contemplated herein are disclosed compounds in combination with at least one other agent that has previously been shown to treat these overweight- or obesity-related conditions.

For example, Type II diabetes has been associated with obesity. Certain complications of Type II diabetes, e.g., disability and premature death, can be prevented, ameliorated, or eliminated by sustained weight loss (Astrup, A. Pub Health Nutr (2001) 4:499-5). Agents administered to treat Type II diabetes include sulfonylureas (e.g., Chlorpropamide, Glipizide, Glyburide, Glimepiride); meglitinides (e.g., Repaglinide and Nateglinide); biguanides (e.g., Metformin); thiazolidinediones (Rosiglitazone, Troglitazone, and Pioglitazone); dipeptidylpeptidase-4 inhibitors (e.g., Sitagliptin, Vildagliptin, and Saxagliptin); glucagon-like peptide-1 mimetics (e.g., Exenatide and Liraglutide); and alpha-glucosidase inhibitors (e.g., Acarbose and Miglitol).

Cardiac disorders and conditions, for example hypertension, dyslipidemia, ischemic heart disease, cardiomyopathy, cardiac infarction, stroke, venous thromboembolic disease and pulmonary hypertension, have been linked to overweight or obesity. For example, hypertension has been linked to obesity because excess adipose tissue secretes substances that are acted on by the kidneys, resulting in hypertension. Additionally, with obesity there are generally higher amounts of insulin produced (because of the excess adipose tissue) and this excess insulin also elevates blood pressure. A major treatment option of hypertension is weight loss. Agents administered to treat hypertension include Chlorthalidone; Hydrochlorothiazide; Indapamide, Metolazone; loop diuretics (e.g., Bumetanide, Ethacrynic acid, Furosemide, Lasix, Torsemide); potassium-sparing agents (e.g., Amiloride hydrochloride, benzamil, Spironolactone, and Triamterene); peripheral agents (e.g., Reserpine); central alpha-agonists (e.g., Clonidine hydrochloride, Guanabenz acetate, Guanfacine hydrochloride, and Methyldopa); alpha-blockers (e.g., Doxazosin mesylate, Prazosin hydrochloride, and Terazosin hydrochloride); beta-blockers (e.g., Acebutolol, Atenolol, Betaxolol, Bisoprolol fumarate, Carteolol hydrochloride, Metoprolol tartrate, Metoprolol succinate, Nadolol, Penbutolol sulfate, Pindolol, Propranolol hydrochloride, and Timolol maleate); combined alpha- and beta-blockers (e.g., Carvedilol and Labetalol hydrochloride); direct vasodilators (e.g., Hydralazine hydrochloride and Minoxidil); calcium antagonists (e.g., Diltiazem hydrochloride and Verapamil hydrochloride); dihydropyridines (e.g., Amlodipine besylate, Felodipine, Isradipine, Nicardipine, Nifedipine, and Nisoldipine); ACE inhibitors (benazepril hydrochloride, Captopril, Enalapril maleate, Fosinopril sodium, Lisinopril, Moexipril, Quinapril hydrochloride, Ramipril, Trandolapril); Angiotensin II receptor blockers (e.g., Losartan potassium, Valsartan, and Irbesartan); Renin inhibitors (e.g., Aliskiren); and combinations thereof. These compounds are administered in regimens and at dosages known in the art.

Carr et al. (The Journal of Clinical Endocrinology & Metabolism (2004) Vol. 89, No. 6 2601-2607) discusses a link between being overweight or obese and dyslipidemia. Dyslipidemia is typically treated with statins. Statins, HMG-CoA reductase inhibitors, slow down production of cholesterol in a subject and/or remove cholesterol buildup from arteries. Statins include mevastatin, lovastatin, pravastatin, simvastatin, velostatin, dihydrocompactin, fluvastatin, atorvastatin, dalvastatin, carvastatin, crilvastatin, bevastatin, cefvastatin, rosuvastatin, pitavastatin, and glenvastatin. These compounds are administered in regimens and at dosages known in the art. Eckel (Circulation (1997) 96:3248-3250) discusses a link between being overweight or obese and ischemic heart disease. Agents administered to treat ischemic heart disease include statins, nitrates (e.g., Isosorbide Dinitrate and Isosorbide Mononitrate), beta-blockers, and calcium channel antagonists. These compounds are administered in regimens and at dosages known in the art.

Wong et al. (Nature Clinical Practice Cardiovascular Medicine (2007) 4:436-443) discusses a link between being overweight or obese and cardiomyopathy. Agents administered to treat cardiomyopathy include inotropic agents (e.g., Digoxin), diuretics (e.g., Furosemide), ACE inhibitors, calcium antagonists, anti-arrhythmic agents (e.g., Sotolol, Amiodarone and Disopyramide), and beta-blockers. These compounds are administered in regimens and at dosages known in the art. Yusef et al. (Lancet (2005) 366(9497):1640-1649) discusses a link between being overweight or obese and cardiac infarction. Agents administered to treat cardiac infarction include ACE inhibitors, Angiotensin II receptor blockers, direct vasodilators, beta blockers, anti-arrhythmic agents and thrombolytic agents (e.g., Alteplase, Retaplase, Tenecteplase, Anistreplase, and Urokinase). These compounds are administered in regimens and at dosages known in the art.

Suk et al. (Stroke (2003) 34:1586-1592) discusses a link between being overweight or obese and strokes. Agents administered to treat strokes include anti-platelet agents (e.g., Aspirin, Clopidogrel, Dipyridamole, and Ticlopidine), anticoagulant agents (e.g., Heparin), and thrombolytic agents. Stein et al. (The American Journal of Medicine (2005) 18(9):978-980) discusses a link between being overweight or obese and venous thromboembolic disease. Agents administered to treat venous thromboembolic disease include anti-platelet agents, anticoagulant agents, and thrombolytic agents. Sztrymf et al. (Rev Pneumol Clin (2002) 58(2):104-10) discusses a link between being overweight or obese and pulmonary hypertension. Agents administered to treat pulmonary hypertension include inotropic agents, anticoagulant agents, diuretics, potassium (e.g., K-dur), vasodilators (e.g., Nifedipine and Diltiazem), Bosentan, Epoprostenol, and Sildenafil. Respiratory disorders and conditions such as obesity-hypoventilation syndrome, asthma, and obstructive sleep apnea, have been linked to being overweight or obese. Elamin (*Chest* (2004) 125:1972-1974) discusses a link between being overweight or obese and asthma. Agents administered to treat asthma include bronchodilators, anti-inflammatory agents, leukotriene blockers, and anti-Ige agents. Particular asthma agents include Zafirlukast, Flunisolide, Triamcinolone, Beclomethasone, Terbutaline, Fluticasone, Formoterol, Beclomethasone, Salmeterol, Theophylline, and Xopenex.

Kessler et al. (Eur Respir J (1996) 9:787-794) discusses a link between being overweight or obese and obstructive sleep apnea. Agents administered to treat sleep apnea include Modafinil and amphetamines.

Hepatic disorders and conditions, such as nonalcoholic fatty liver disease, have been linked to being overweight or obese. Tolman et al. (Ther Clin Risk Manag (2007) 6:1153-1163) discusses a link between being overweight or obese and nonalcoholic fatty liver disease. Agents administered to treat nonalcoholic fatty liver disease include antioxidants (e.g., Vitamins E and C), insulin sensitizers (Metformin, Pioglitazone, Rosiglitazone, and Betaine), hepatoprotectants, and lipid-lowering agents.

Skeletal disorders and conditions, such as, back pain and osteoarthritis of weight-bearing joints, have been linked to being overweight or obese. van Saase (J Rheumatol (1988) 15(7):1152-1158) discusses a link between being overweight or obese and osteoarthritis of weight-bearing joints. Agents administered to treat osteoarthritis of weight-bearing joints include Acetaminophen, non-steroidal anti-inflammatory agents (e.g., Ibuprofen, Etodolac, Oxaprozin, Naproxen, Diclofenac, and Nabumetone), COX-2 inhibitors (e.g., Celecoxib), steroids, supplements (e.g. glucosamine and chondroitin sulfate), and artificial joint fluid.

Metabolic disorders and conditions, for example, Prader-Willi Syndrome and polycystic ovary syndrome, have been linked to being overweight or obese. Cassidy (Journal of Medical Genetics (1997) 34:917-923) discusses a link between being overweight or obese and Prader-Willi Syndrome. Agents administered to treat Prader-Willi Syndrome include human growth hormone (HGH), somatropin, and weight loss agents (e.g., Orlistat, Sibutramine, Methamphetamine, Ionamin, Phentermine, Bupropion, Diethylpropion, Phendimetrazine, Benzphetermine, and Topamax).

Hoeger (Obstetrics and Gynecology Clinics of North America (2001) 28(1):85-97) discusses a link between being overweight or obese and polycystic ovary syndrome. Agents administered to treat polycystic ovary syndrome include insulin-sensitizers, combinations of synthetic estrogen and progesterone, Spironolactone, Eflornithine, and Clomiphene. Reproductive disorders and conditions such as sexual dysfunction, erectile dysfunction, infertility, obstetric complications, and fetal abnormalities, have been linked to being overweight or obese. Larsen et al. (Int J Obes (Lond) (2007) 8:1189-1198) discusses a link between being overweight or obese and sexual dysfunction. Chung et al. (Eur Urol (1999) 36(1):68-70) discusses a link between being overweight or obese and erectile dysfunction. Agents administered to treat erectile dysfunction include phosphodiesterase inhibitors (e.g., Tadalafil, Sildenafil citrate, and Vardenafil), prostaglandin E analogs (e.g., Alprostadil), alkaloids (e.g., Yohimbine), and testosterone. Pasquali et al. (Hum Reprod (1997) 1:82-87) discusses a link between being overweight or obese and infertility. Agents administered to treat infertility include Clomiphene, Clomiphene citrate, Bromocriptine, Gonadotropin-releasing Hormone (GnRH), GnRH agonist, GnRH antagonist, Tamoxifen/nolvadex, gonadotropins, Human Chorionic Gonadotropin (HCG), Human Menopausal Gonadotropin (HmG), progesterone, recombinant follicle stimulating hormone (FSH), Urofollitropin, Heparin, Follitropin alfa, and Follitropin beta.

Weiss et al. (American Journal of Obstetrics and Gynecology (2004) 190(4): 1091-1097) discusses a link between being overweight or obese and obstetric complications. Agents administered to treat obstetric complications include Bupivacaine hydrochloride, Dinoprostone PGE2, Meperidine HCl, Ferro-folic-500/iberet-folic-500, Meperidine, Methylergonovine maleate, Ropivacaine HCl, Nalbuphine HCl, Oxymorphone HCl, Oxytocin, Dinoprostone, Ritodrine, Scopolamine hydrobromide, Sufentanil citrate, and Oxytocic.

Psychiatric disorders and conditions, for example, weight-associated depression and anxiety, have been linked to being overweight or obese. Dixson et al. (Arch Intern Med (2003) 163:2058-2065) discusses a link between being overweight or obese and depression. Agents administered to treat depression include serotonin reuptake inhibitors (e.g., Fluoxetine, Escitalopram, Citalopram, Paroxetine, Sertraline, and Venlafaxine); tricyclic antidepressants (e.g., Amitriptyline, Amoxapine, Clomipramine, Desipramine, Dosulepin hydrochloride, Doxepin, Imipramine, Iprindole, Lofepramine, Nortriptyline, Opipramol, Protriptyline, and Trimipramine); monoamine oxidase inhibitors (e.g., Isocarboxazid, Moclobemide, Phenelzine, Tranylcypromine, Selegiline, Rasagiline, Nialamide, Iproniazid, Iproclozide, Toloxatone, Linezolid, Dienolide kavapyrone desmethoxyyangonin, and Dextroamphetamine); psychostimulants (e.g., Amphetamine, Methamphetamine, Methylphenidate, and Arecoline); antipsychotics (e.g., Butyrophenones, Phenothiazines, Thioxanthenes, Clozapine, Olanzapine, Risperidone, Quetiapine, Ziprasidone, Amisulpride, Paliperidone, Symbyax, Tetrabenazine, and Cannabidiol); and mood stabilizers (e.g., Lithium carbonate, Valproic acid, Divalproex sodium, Sodium valproate, Lamotrigine, Carbamazepine, Gabapentin, Oxcarbazepine, and Topiramate).

Simon et al. (Archives of General Psychiatry (2006) 63(7):824-830) discusses a link between being overweight or obese and anxiety. Agents administered to treat anxiety include serotonin reuptake inhibitors, mood stabilizers, benzodiazepines (e.g., Alprazolam, Clonazepam, Diazepam, and Lorazepam), tricyclic antidepressants, monoamine oxidase inhibitors, and beta-blockers.

Another aspect of the invention provides methods for facilitating and maintaining weight loss in a subject involving administering to the subject an amount of a disclosed compound effective to result in weight loss in the subject; and administering a therapeutically effective amount of a different weight loss agent to maintain a reduced weight in the subject. Weight loss agents include serotonin and noradrenergic re-uptake inhibitors; noradrenergic re-uptake inhibitors; selective serotonin re-uptake inhibitors; and intestinal lipase inhibitors. Particular weight loss agents include orlistat, sibutramine, methamphetamine, ionamin, phenterminc, bupropion, diethylpropion, phendimetrazine, benzpheterminc, bromocriptine, lorcaserin, topiramate, or agents acting to modulate food intake by blocking ghrelin action, inhibiting diacylglycerol acyltransferase 1 (DGAT1) activity, inhibiting stearoyl CoA desaturase 1 (SCD1) activity, inhibiting neuropeptide Y receptor 1 function, activating neuropeptide Y receptor 2 or 4 function, or inhibiting activity of sodium-glucose cotransporters 1 or 2. These compounds are administered in regimens and at dosages known in the art.

EXAMPLES

The compounds described herein can be prepared in a number of ways based on the teachings contained herein and synthetic procedures known in the art. In the description of the synthetic methods described below, it is to be understood that all proposed reaction conditions, including choice of solvent, reaction atmosphere, reaction temperature, duration of the experiment and workup procedures, can be chosen to be the conditions standard for that reaction, unless otherwise indicated. It is understood by one skilled in the art of organic synthesis that the functionality present on various portions of the molecule should be compatible with the reagents and reactions proposed. Substituents not compatible with the reaction conditions will be apparent to one skilled in the art, and alternate methods are therefore indicated. The starting materials for the examples are either commercially available or are readily prepared by standard methods from known materials.

At least some of the compounds identified as "Intermediates" herein are contemplated as compounds of the invention.

$^1$H NMR spectra were recorded at ambient temperature using a Varian Unity Inova (400 MHz) spectrometer with a triple resonance 5 mm probe for Example compounds, and either a Bruker Avance DRX (400 MHz) spectrometer or a Bruker Avance DPX (300 MHz) spectrometer for Intermediate compounds. Chemical shifts are expressed in ppm relative to tetramethylsilane. The following abbreviations have been used: br=broad signal, s=singlet, d=doublet, dd=double doublet, dt=double triplet, t=triplet, q=quartet, m=multiplet.

Mass Spectrometry (LCMS) experiments to determine retention times and associated mass ions were performed using the following methods:

Method A: Experiments were performed on a Waters V G Platform II quadrupole spectrometer linked to a Hewlett Packard 1050 LC system with a diode array detector. The spectrometer has an electrospray source operating in positive and negative ion mode. Additional detection was achieved using a Sedex 85 evaporative light scattering detector. LC was carried out using a Luna 3 micron 30×4.6 mm C18 column and a 2 mL/minute flow rate. The initial solvent system was 95% water containing 0.1% formic acid (solvent A) and 5% acetonitrile containing 0.1% formic acid (solvent B) for the first 0.3 minute followed by a gradient up to 5% solvent A and 95% solvent B over the next 4 minutes. The final solvent system was held constant for a further 1 minute.

Method B: Experiments were performed on a Waters Micromass ZQ2000 quadrapole mass spectrometer linked to a Waters Acquity UPLC system with a PDA UV detector. The spectrometer has an electrospray source operating in positive and negative ion mode. LC was carried out using an Acquity BEH 1.7 micron C18 column, an Acquity BEH Shield 1.7 micron RP18 column or an Acquity HSST 1.8 micron column. Each column has dimensions of 100×2.1 mm and was maintained at 40° C. with a flow rate of 0.4 mL/minute. The initial solvent system was 95% water containing 0.1% formic acid (solvent A) and 5% acetonitrile containing 0.1% formic acid (solvent B) for the first 0.4 minute followed by a gradient up to 5% solvent A and 95% solvent B over the next 6 minutes. The final solvent system was held constant for a further 0.8 minutes.

Microwave experiments were carried out using a Biotage Initiator™, which uses a single-mode resonator and dynamic field tuning. Temperatures from 40-250° C. can be achieved, and pressures of up to 20 bars can be reached. A facility exists to apply air cooling during the irradiation.

Preparative HPLC purification was carried out using either a C18-reverse-phase column from Genesis (C18) or a C6-phenyl column from Phenomenex (C6-phenyl) (100× 22.5 mm i.d. with 7 micron particle size, UV detection at 230 or 254 nm, flow 5-15 mL/min), eluting with gradients from 100-0 to 0-100% water/acetonitrile or water/methanol containing 0.1% formic acid. Fractions containing the required product (identified by LCMS analysis) were pooled, the organic fraction removed by evaporation, and the remaining aqueous fraction lyophilised, to give the product.

Compounds which required column chromatography were purified manually or fully automatically using either a Biotage SP1™ Flash Purification system with Touch Logic Control™ or a Combiflash Companion® with pre-packed silica gel Isolute® SPE cartridge, Biotage SNAP cartridge or Redisep® Rf cartridge respectively.

ABBREVIATIONS

DCM: Dichloromethane
DMSO: Dimethylsulfoxide
THF: Tetrahydrofuran
TBME: tert-Butyl methyl ether
DMAP: 4-Dimethylaminopyridine

Example 1

Cis-(1aRS,7bSR)-5-[2-((Z)-3-diethylaminoprop-1-enyl)-4-fluoro-benzenesulfonylmethyl]-1,1a,2,7b-tetrahydrocyclopropa[c]chromene-4-carboxylic acid

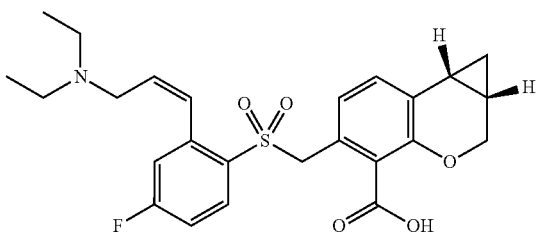

Mixture of enantiomers

A mixture of methyl cis-(1aRS,7bSR)-5-[2-((Z)-3-diethylaminoprop-1-enyl)-4-fluoro-benzenesulfonylmethyl]-1,1a,2,7b-tetrahydrocyclopropa[c]chromene-4-carboxylate (Intermediate 1, 0.72 g) and lithium hydroxide (0.622 g) in dioxane (20 mL) and water (5 mL) was stirred and heated at 80° C. for 5 hours. After cooling, the mixture was filtered and the filtrate was concentrated to low volume under vacuum. The aqueous residue was acidified with formic acid to pH 5 and extracted with DCM. The organic layer was dried (MgSO₄) and filtered. The filtrate was evaporated to dryness and the residue was purified by reverse phase chromatography using a C-18 5 micron cartridge and eluting with a mixture of methanol and water, with a gradient of 10-98%. The product was repurified by HPLC(C18) eluting with a mixture of acetonitrile and water (containing 0.1% formic acid) to give cis-(1aRS,7bSR)-5-[2-((Z)-3-diethylaminoprop-1-enyl)-4-fluorobenzenesulfonylmethyl]-1,1a,2,7b-tetrahydrocyclopropa[c]chromene-4-carboxylic acid (0.125 g) as a white solid.

$^1$H NMR (DMSO) δ: 7.45 (1H, dd), 7.36 (1H, d), 7.21 (2H, d), 7.06 (1H, d), 6.87 (1H, d), 6.22 (1H, m), 4.61 (2H, s), 4.08 (1H, d), 3.81 (2H, d), 3.50 (1H, d), 2.99 (4H, q), 1.91 (1H, m), 1.70 (1H, m), 1.09 (6H, t), 0.93 (1H, m), 0.72 (1H, m).

LCMS (Method B): r/t 2.96 (M+H) 474.

Examples 2 and 3

Separation of Enantiomers from Example 1

Sample from Example 1 was subjected to chiral separation using a Chiralpak IC column, 10 mm×250 mm, particle size 5 micron. Eluting solvent ethanol: TBME (20%).

Example 2

First Eluting Enantiomer: r/t on Analytical Column (4.6 mm×250 mm): 8.5 Minutes >98% ee $^1$H NMR (CDCl₃) δ: 7.77 (1H, d), 7.46 (1H, dd), 7.11 (1H, d), 7.03 (1H, d), 6.89 (1H, dt), 6.79 (1H, dd), 5.99 (1H, m), 5.2-4.8 (1H, br s), 4.7-4.3 (1H, br s), 4.3-3.0 (2H, br), 4.22 (1H, d), 3.67 (1H, br s), 3.12 (4H, m), 1.87 (1H, m), 1.62 (1H, m), 1.24 (6H, t), 1.06 (1H, m), 0.92 (1H, m).

LCMS (Method B): r/t 2.95 (M+H) 474.

Example 3

Second Eluting Enantiomer: r/t on Analytical Column (4.6 mm×250 mm): 11.8 Minutes >98% ee $^1$H NMR (CDCl₃) δ: 7.77 (1H, d), 7.46 (1H, dd), 7.11 (1H, d), 7.03 (1H, d), 6.89 (1H, dt), 6.79 (1H, dd), 5.99 (1H, m), 5.2-4.8 (1H, br s), 4.7-4.3 (1H, br s), 4.3-3.0 (2H, br) 4.22 (1H, d), 3.67 (1H, br s), 3.12 (4H, m), 1.87 (1H, m), 1.62 (1H, m), 1.24 (6H, t), 1.06 (1H, m), 0.92 (1H, m).

LCMS (Method B): r/t 2.96 (M+H) 474.

Intermediate 1

Methyl cis-(1aRS,7bSR)-5-[2-((Z)-3-diethylaminoprop-1-enyl)-4-fluorobenzenesulfonylmethyl]-1,1a,2,7b-tetrahydrocyclopropa[c]chromene-4-carboxylate

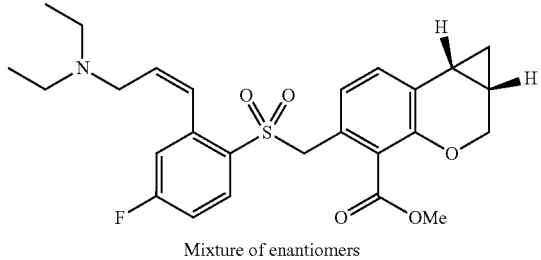 [SMILES: CCN(CC)C/C=C\c1cc(F)ccc1S(=O)(=O)Cc1ccc2c(c1C(=O)OC)OC[C@H]1C[C@@H]21]

Mixture of enantiomers

A mixture of methyl cis-(1aRS,7bSR)-5-(2-bromo-4-fluorobenzenesulfonylmethyl)-1,1a,2,7b-tetrahydrocyclopropa[c]chromene-4-carboxylate (Intermediate 5, 0.66 g), N,N-diethyl-N—((Z)-1-tributylstannanylprop-1-en-3-yl)amine (Intermediate 2, 1.17 g), tri-tert-butylphosphonium tetrafluoroborate (0.145 g), Iris-(dibenzylideneacetone)-dipalladium (0.066 g) in dioxane (16 mL) and DMSO (1.6 mL) was degassed and purged with nitrogen, then heated at 100° C. for 1.5 hours. After cooling, the mixture was poured into brine and extracted with ethyl acetate. The organic layer was dried (MgSO₄) and filtered. The filtrate was evaporated to dryness and the residue was purified by chromatography on silica, eluting with a mixture of methanol and DCM with a gradient of 0-15% to give methyl cis-(1aRS,7bSR)-5-[2-((Z)-3-diethylaminoprop-1-enyl)-4-fluorobenzenesulfonylmethyl]-1,1a,2,7b-tetrahydrocyclopropa[c]chromene-4-carboxylate (0.72 g) as a glass.

LCMS (Method A) r/t 2.20 (M+H) 488.

Intermediate 2

N,N-Diethyl-N—((Z)-1-tributylstannanylprop-1-en-3-yl)-amine

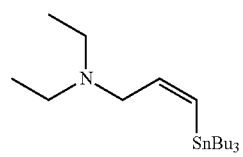

Diethylamine (19 mL) was added to a solution of ((Z)-3-bromoprop-1-enyl)tributyl-stannane (Intermediate 3, 7.52 g) in THF (60 mL) and the mixture was stirred for 3 hours. The reaction mixture was evaporated to dryness and the residue was purified by chromatography on a silica column which had been pre-washed with 20% triethylamine in acetonitrile. The column was eluted with a mixture of ethyl acetate and pentane with a gradient of 0-10% to give N,N-diethyl-N—((Z)-1-tributylstannanylprop-1-en-3-yl)amine (4.75 g) as an orange oil.

$^1$H NMR (CDCl₃) δ: 6.59 (1H, dt), 5.97 (1H, dt), 3.08 (2H, dd), 2.53 (4H, q), 1.49 (6H, m), 1.37-1.24 (6H, m), 1.04 (6H, t), 0.92-0.89 (15H, m).

Intermediate 3

((Z)-3-Bromoprop-1-enyl)tributylstannane

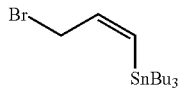

A solution of triphenylphosphine (5.32 g) in DCM (60 mL) was added to a solution of (Z)-3-tributylstannanylprop-2-en-1-ol (Intermediate 4, 6.4 g) and carbon tetrabromide (9.18 g) in DCM (60 mL) and the mixture was stirred for 2.5 hours. The mixture was evaporated to low volume and pentane was added. The solids were removed by filtration and the filtrate was evaporated to dryness. Pentane was added and the solids were again removed by filtration and the filtrate was evaporated to dryness to give ((Z)-3-bromoprop-1-enyl)tributylstannane (12.14 g) as an oil.

$^1$H NMR (CDCl$_3$) δ: 6.71 (1H, dt), 6.11 (1H, d), 3.88 (2H, d), 1.52-1.50 (6H, m), 1.37-1.27 (6H, m), 0.99-0.97 (6H, m), 0.90 (9H, t).

Intermediate 4

(Z)-3-Tributylstannanylprop-2-en-1-ol

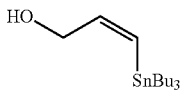

Propargyl alcohol (5 mL) was added to a solution of lithium aluminium hydride (1M in THF, 43 mL) in THF (70 mL) at −78° C. The resultant mixture was warmed to room temperature and stirred for 18 hours. It was re-cooled to −78° C. and a solution of tri-n-butyl tin chloride (8.32 mL) in diethyl ether (50 mL) was added and the mixture was stirred for 3 hours whilst gradually warming to room temperature. The reaction mixture was cooled to −5° C. and quenched by addition of water and 15% aqueous sodium hydroxide solution then warmed to room temperature. Ethyl acetate was added and the mixture was stirred for 1 hour. The mixture was filtered through Celite and the filtrate was evaporated to dryness. The residue was purified by chromatography on a silica column which had been pre-washed with 20% triethylamine in acetonitrile. The column was eluted with a mixture of ethyl acetate and pentane with a gradient of 0-10% to give (Z)-3-tributylstannanyl-prop-2-en-1-ol (5.06 g) as a clear oil.

$^1$H NMR (CDCl$_3$) δ: 6.70 (1H, dt), 6.08 (1H, dt), 4.12 (2H, dd), 1.49 (6H, m), 1.31 (6H, m), 0.98-0.84 (15H, m).

Intermediate 5

Methyl cis-(1aRS,7bSR)-5-(2-bromo-4-fluorobenzenesulfonyl-methyl)-1,1a,2,7b-tetrahydrocyclopropa[c]chromene-4-carboxylate

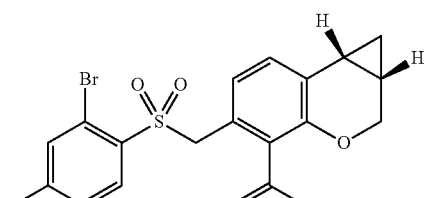

Mixture of enantiomers

A mixture of methyl cis-(1aRS,7bSR)-5-chloromethyl-1,1a,2,7b-tetrahydro-cyclopropa[c]chromene-4-carboxylate (Intermediate 6, 0.486 g), 2-bromo-4-fluorothiophenol (0.478 g), potassium carbonate (0.828 g) and potassium iodide (0.01 g) in THF (20 mL) was stirred and heated at 60° C. for 2 hours. After cooling, the mixture was partitioned between ethyl acetate and brine. The organic layer was dried (MgSO$_4$) and filtered. The filtrate was evaporated to dryness and the residue was dissolved in acetic acid (20 mL) and treated with hydrogen peroxide (50%, 5 mL). The resultant mixture was stirred at room temperature for 48 hours. Water was added and the mixture was extracted with ethyl acetate, washed with saturated aqueous sodium bicarbonate solution, dried (MgSO$_4$) and filtered. The filtrate was evaporated to dryness and the residue was purified by chromatography on silica, eluting with a mixture of ethyl acetate and pentane with a gradient of 0-100% to give methyl cis-(1aRS,7bSR)-5-(2-bromo-4-fluorobenzencsulfonylmethyl)-1,1a,2,7b-tetrahydrocyclopropa[c]chromene-4-carboxylate (0.781 g) as a colourless glass.

$^1$H NMR (CDCl$_3$) δ: 7.87 (1H, dd), 7.50 (1H, dd), 7.17 (1H, d), 7.07 (H, dt), 6.74 (1H, d), 4.85 (1H, d), 4.75 (1H, d), 4.34 (1H, d), 3.89 (3H, s), 3.83 (1H, d), 1.95 (1H, m), 1.76 (1H, m), 1.08 (2H, m).

Intermediate 6

Methyl cis-(1aRS,7bSR)-5-chloromethyl-1,1a,2,7b-tetrahydro-cyclopropa[c]chromene-4-carboxylate

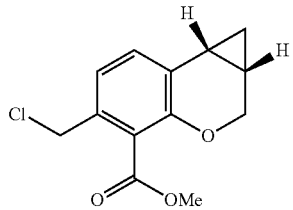

Mixture of enantiomers

Zinc chloride (0.014 g) was added to a solution of methyl cis-(1aRS,7bSR)-5-methoxymethyl-1,1a,2,7b-tetrahydrocyclopropa[c]chromene-4-carboxylate (Intermediate 7, 0.53 g) and acetyl chloride (0.77 mL) in anhydrous diethyl ether (50 mL) and the resultant mixture was stirred for 1.5 hours. The mixture was washed with water, dried (MgSO$_4$) and filtered. The filtrate was evaporated to dryness to give methyl cis-(1aRS,7bSR)-5-chloromethyl-1,1a,2,7b-tetrahydro-cyclopropa[c]chromene-4-carboxylate (0.486 g) as a gum.

$^1$H NMR (CDCl$_3$) δ: 7.25 (1H, d), 6.94 (1H, d), 4.61 (1H, d), 4.56 (1H, d), 4.37 (1H, d), 3.93 (3H, s), 3.87 (1H, d), 1.99 (1H, m), 1.76 (1H, m), 1.12 (1H, m), 1.07 (1H, m).

Intermediate 7

Methyl cis-(1aRS,7bSR)-5-methoxymethyl-1,1a,2,7b-tetrahydro-cyclopropa[c]chromene-4-carboxylate

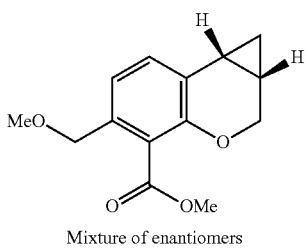

Mixture of enantiomers

A mixture of methyl cis-(1aRS,7bSR)-1,1-dibromo-5-methoxymethyl-1,1a,2,7b-tetrahydrocyclopropa[c]chromene-4-carboxylate (Intermediate 8, 1.06 g), zinc dust (4.14 g), and ammonium chloride (1.75 g) in absolute ethanol (100 mL) was stirred and heated at reflux for 6 hours. Further zinc dust (2.0 g) and ammonium chloride (0.9 g) were added and the mixture was stirred and heated at reflux overnight. After cooling, the mixture was filtered through Celite and the filtrate was evaporated to dryness. The residue was partitioned between DCM and water and the organic layer was dried (MgSO$_4$) and filtered. The filtrate was evaporated to dryness to give methyl cis-(1aRS,7bSR)-5-methoxymethyl-1,1a,2,7b-tetrahydrocyclopropa[c]chromene-4-carboxylate (0.63 g) as an oil.

$^1$H NMR (CDCl$_3$) δ: 7.24 (1H, d), 6.89 (1H, d), 4.44 (1H, d), 4.40 (1H, d), 4.36 (1H, d), 3.89 (3H, s), 3.87 (1H, d), 3.31 (3H, s), 1.98 (1H, m), 1.74 (1H, m), 1.10 (1H, m), 1.04 (1H, m).

Intermediate 8

Methyl cis-(1aRS,7bSR)-1,1-dibromo-5-methoxymethyl-1,1a,2,7b-tetrahydrocyclopropa[c]chromene-4-carboxylate

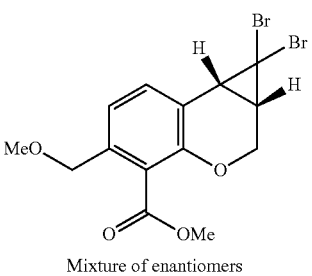 [SMILES: COCc1ccc2c(c1C(=O)OC)OC[C@@H]1[C@H]2C1(Br)Br]

Mixture of enantiomers

Aqueous sodium hydroxide solution (50% w/v, 1.63 mL) was added slowly to a vigorously stirred mixture of methyl 7-methoxymethyl-2H-chromene-8-carboxylate (Intermediate 9, 0.875 g), benzyltriethylammonium chloride (0.173 g) and bromoform (15 mL). The resultant mixture was vigorously stirred and heated at 60° C. for 3 hours. After cooling, the mixture was poured into a mixture of brine and ethyl acetate. The aqueous layer was further extracted with ethyl acetate and the combined organic layers were dried (MgSO$_4$) and filtered. The filtrate was evaporated to dryness and the residue was purified by chromatography on silica, eluting with a mixture of TBME and cyclohexane with a gradient of 0-35% to give methyl cis-(1aRS,7bSR)-1,1-dibromo-5-methoxymethyl-1,1a,2,7b-tetrahydrocyclopropa[c]chromene-4-carboxylate (1.06 g) as a white solid.

$^1$H NMR (CDCl$_3$) δ: 7.37 (1H, d), 6.98 (1H, d), 4.50-4.40 (3H, m), 4.35 (1H, dd), 3.87 (3H, s), 3.33 (3H, s), 2.91 (1H, d), 2.45 (1H, m).

Intermediate 9

Methyl 7-methoxymethyl-2H-chromene-8-carboxylate

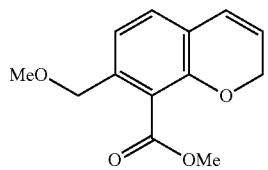 [SMILES: COCc1ccc2c(c1C(=O)OC)OCC=C2]

A mixture of methyl 2-methoxymethyl-6-propargyloxybenzoate (Intermediate 10, 1.4 g) and [Bis-(trifluoromethanesulfonyl)imidate](triphenyl phosphine) gold 2:1 complex with toluene (0.188 g) in toluene (40 mL) was stirred and heated under an atmosphere of nitrogen overnight. After cooling, the mixture was filtered through Celite and the filtrate was evaporated to dryness. The residue was purified by chromatography on silica, eluting with a mixture of TBME and cyclohexane with a gradient of 0-30% to give methyl 7-methoxymethyl-2H-chromene-8-carboxylate (0.875 g) as an oil.

$^1$H NMR (CDCl$_3$) δ: 6.96 (1H, d), 6.86 (1H, d), 6.40 (1H, dt), 5.79 (1H, m), 4.86 (2H, dd), 4.43 (2H, s), 3.89 (3H, s), 3.32 (3H, s).

Intermediate 10

Methyl 2-methoxymethyl-6-propargyloxybenzoate

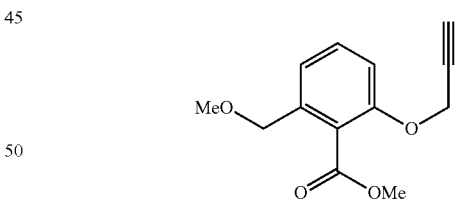

A mixture of methyl 2-hydroxy-6-methoxymethylbenzoate (Intermediate 11, 1.46 g), propargyl bromide (80% solution in toluene, 1.24 mL) and potassium carbonate (1.55 g) in acetone (50 mL) was stirred and heated at reflux for 2 hours. Further propargyl bromide (80% solution in toluene, 0.9 mL) was added and the mixture was stirred and heated at reflux for 2 hours. After cooling, the mixture was filtered and the filtrate was evaporated to dryness. The residue was purified by chromatography on silica, eluting with a mixture of ethyl acetate and pentane with a gradient of 0-30% to give methyl 2-methoxymethyl-6-propargyloxybenzoate (1.34 g) as an oil.

$^1$H NMR (CDCl$_3$) δ: 7.35 (1H, t), 7.04 (2H, d), 4.72 (2H, d), 4.47 (2H, s), 3.91 (3H, s), 3.34 (3H, s), 2.50 (1H, t).

Intermediate 11

Methyl 2-hydroxy-6-methoxymethylbenzoate

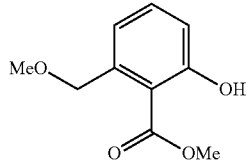 [SMILES: COCc1cccc(O)c1C(=O)OC]

A solution of methyl 2-bromomethyl-6-(tert-butyldimethylsilyloxy)benzoate (Intermediate 12, 4.26 g) in methanol (63 mL) was stirred and heated at reflux overnight. After cooling, the mixture was basified by addition of solid sodium bicarbonate and then evaporated to dryness. The residue was triturated with DCM and filtered. The filtrate was evaporated to dryness and the residue was purified by chromatography on silica, eluting with a mixture of ethyl acetate and cyclohexane with a gradient of 0-25% to give methyl 2-hydroxy-6-methoxymethylbenzoate (1.46 g) as a white crystalline solid.

$^1$H NMR (CDCl$_3$) δ: 11.10 (1H, s), 7.42 (1H, t), 7.11 (1H, d), 6.94 (1H, d), 4.71 (2H, s), 3.98 (3H, s), 3.44 (3H, s).

Intermediate 12

Methyl 2-bromomethyl-6-(tert-butyldimethylsilyloxy)benzoate

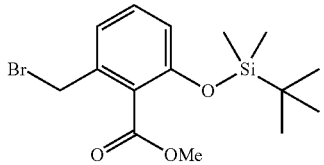 [SMILES: COC(=O)c1c(CBr)cccc1O[Si](C)(C)C(C)(C)C]

N-Bromosuccinimide (7.6 g) was added to a solution of methyl 2-(tert-butyldimethylsilyloxy)-6-methylbenzoate (Intermediate 13, 11.9 g) in carbon tetrachloride (150 mL) and the mixture was stirred and heated to reflux. Azo-bis-isobutyronitrile (0.1 g) was added and the mixture was illuminated with a 500 W tungsten filament lamp for 2 hours. The mixture was cooled and left to stand overnight then filtered through a 25 g silica cartridge eluting with a mixture of ethyl acetate and pentane (20%). The eluent was evaporated to dryness and the residue was redissolved in carbon tetrachloride (150 mL) and N-bromosuccinimide (6.96 g) was added. The mixture was heated to reflux and azo-bis-isobutyronitrile (0.1 g) was added. The resultant mixture was illuminated with a 500 W tungsten filament lamp overnight. After cooling, the mixture was filtered and the solid was washed with pentane. The combined organic solutions were evaporated to dryness and the residue was purified by chromatography on silica, eluting with a mixture of TBME and pentane with a gradient of 0-10% to give methyl 2-bromomethyl-6-(tert-butyldimethylsilyloxy)benzoate (4.99 g) as a yellow oil.

$^1$H NMR (CDCl$_3$) δ: 7.23 (1H, t), 6.99 (1H, d), 6.80 (1H, d), 4.51 (2H, s), 3.92 (3H, s), 0.97 (9H, s), 0.22 (6H, s).

Intermediate 13

Methyl 2-(tert-butyldimethylsilyloxy)-6-methylbenzoate

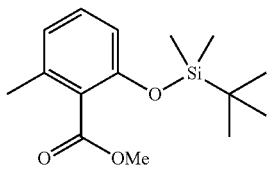 [SMILES: COC(=O)c1c(C)cccc1O[Si](C)(C)C(C)(C)C]

A mixture of methyl 2-hydroxy-6-methylbenzoate (prepared according to Doehner et al, WO 01/05739, 10.0 g), tert-butyldimethylsilyl chloride (11.0 g), N,N-di-isopropylethylamine (32 mL) and DMAP (0.75 g) in DCM (400 mL) was stirred at room temperature overnight. The mixture was washed with water and brine, dried (MgSO$_4$) and filtered. The filtrate was evaporated to dryness and the residue was purified by chromatography on silica eluting with a mixture of ethyl acetate and pentane with a gradient of 0-10% to give methyl 2-(tert-butyldimethylsilyloxy)-6-methylbenzoate (11.9 g) as an oil.

$^1$H NMR (CDCl$_3$) δ: 7.13 (1H, t), 6.78 (1H, d), 6.66 (1H, d), 3.87 (3H, s), 2.27 (3H, s), 0.96 (9H, s), 0.21 (6H, s).

Biological Example

Compounds are tested for their capacity to inhibit recombinant human MetAP2 activity using the following assay.

Human recombinant MetAP2 expressed in Sf9 cells followed by affinity purification and EDTA treatment to remove endogenous active site cation was dialysed against MnCl$_2$ to produce the manganese enzyme used in the assay. The assay was carried out for 30 minutes at 25° C. in 50 mM HEPES buffer containing 100 mM NaCl, at pH 7.5. The presence of 0.75 mM Methionine-Alanine-Serine (MAS) substrate and 50 μg/mL amino acid oxidase using a dilution of purified MetAP2 gives >3-fold signal:noise. Cleavage of the substrate by MetAP2 and oxidation of free methionine by amino acid oxidase was detected and quantified using fluorescence generated by Amplex red (10-acetyl-3,7-dihydroxyphenoxazine) in combination with horseradish peroxidase which detects H$_2$O$_2$ released during the oxidation step. The fluorescent signal was detected using a multiwell fluorimeter. Compounds were diluted in DMSO prior to addition to assay buffer, the final DMSO concentration in the assay being 1%.

The IC$_{50}$ is defined as the concentration at which a given compound achieves 50% inhibition of control. IC$_{50}$ values are calculated using the XLfit software package (version 2.0.5).

Compounds of the invention demonstrated activity in the assay of this Example as indicated in the following table, wherein A represents <0.1 μM, B represents IC$_{50}$>0.1 μM.

| Compound name | Activity |
| --- | --- |
| Cis-(1aRS,7bSR)-5-[2-((Z)-3-diethylaminoprop-1-enyl)-4-fluoro-benzenesulfonylmethyl]-1,1a,2,7b-tetrahydrocyclopropa[c]-chromene-4-carboxylic | B |
| First eluting enantiomer of cis-(1aRS,7bSR)-5-[2-((Z)-3-diethylaminoprop-1-enyl)-4-fluoro-benzenesulfonylmethyl]-1,1a,2,7b-tetrahydrocyclopropa[c]chromene-4-carboxylic | B |

-continued

| Compound name | Activity |
|---|---|
| Second eluting enantiomer of cis-(1aRS,7bSR)-5-[2-((Z)-3-diethylaminoprop-1-enyl)-4-fluoro-benzenesulfonylmethyl]-1,1a,2,7b-tetrahydrocyclopropa[c]chromene-4-carboxylic | A |

INCORPORATION BY REFERENCE

All publications and patents mentioned herein, including those items listed below, are hereby incorporated by reference in their entirety for all purposes as if each individual publication or patent was specifically and individually incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present invention.

What is claimed is:
1. A tricyclic compound represented by:

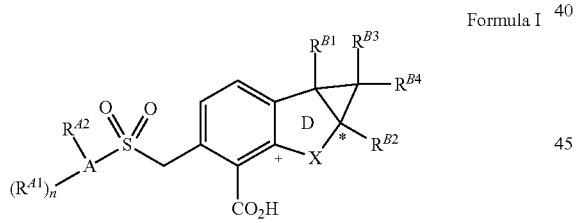

Formula I wherein:
D is a 5-7 membered heterocyclic or carbocyclic ring;
X is selected from the group consisting of: $^+$—C($R^{D1}R^{D2}$)—C($R^{D5}R^{D6}$)-*, $^+$—$W^1$—C($R^{D5}R^{D6}$)—*, $^+$—$W^1$—C(O)-*, $^+$—C($R^{D1}R^{D2}$)—$W^3$—*, $^+$—C($R^{D1}R^{D2}$)—C($R^{D3}R^{D4}$)—C($R^{D5}R^{D6}$)-*, $^+$—$W^1$—C($R^{D3}R^{D4}$)—C($R^{D5}R^{D6}$)-*, $^+$—$W^1$—C(O)—C($R^{D5}R^{D6}$)-*, $^+$—C($R^{D1}R^{D2}$)—$W^2$—C($R^{D5}R^{D6}$)-*, $^+$—C($R^{D1}R^{D2}$)—$W^2$—C(O)—*, $^+$—C($R^{D1}R^{D2}$)—C($R^{D3}R^{D4}$)—$W^3$—*, and $^+$—C($R^{D1}R^{D2}$)—C(O)—$W^3$—*, in which the attachment points are indicated by $^+$ and * in X and in Formula I;
$W^1$ is selected from the group consisting of: O and N($R^{N1}$);
$W^2$ is selected from the group consisting of: O and N($R^{N2}$);
$W^3$ is selected from the group consisting of: O and N($R^{N3}$);

$R^{B1}$ and $R^{B2}$ are each independently selected from the group consisting of hydrogen, fluorine, hydroxyl, CN, $C_{1-3}$alkyl and $C_{1-2}$alkoxy; wherein $C_{1-3}$alkyl and $C_{1-2}$alkoxy may be optionally substituted by one or more fluorine atoms or a moiety selected from the group consisting of cyano, hydroxyl and $C_{1-2}$alkoxy;
$R^{B3}$ and $R^{B4}$ are each independently selected from the group consisting of hydrogen, fluorine and $C_{1-2}$alkyl; wherein $C_{1-2}$alkyl may be optionally substituted by one or more fluorine atoms;
A is a ring selected from the group consisting of: phenyl, a 5-6 membered heteroaryl having 1, 2 or 3 heteroatoms each selected from the group consisting of S, N and O, and a 4-7 membered heterocycle having 1, 2 or 3 heteroatoms each selected from the group consisting of N and O;
$R^{A1}$ is selected, independently for each occurrence, from the group consisting of: hydrogen, hydroxyl, cyano, halogen, $C_{1-4}$alkyl and $C_{1-3}$alkoxy; wherein $C_{1-4}$alkyl and $C_{1-3}$alkoxy may be optionally substituted by one or more fluorines;
$R^{A2}$ is selected from the group consisting of: hydrogen, $R^iR^jN$—, heterocyclyl, heterocyclyloxy, and heterocyclyl-(NR$^a$)—; wherein said heterocyclyl may optionally be substituted by one or more substituents selected from R$^g$; and wherein if said heterocyclyl contains a —NH moiety that nitrogen may optionally be substituted by one or more groups R$^h$; or
$R^{A2}$ is selected from the group consisting of: $C_{1-6}$alkyl, $C_{2-6}$alkenyl, $C_{2-6}$alkynyl, $C_{3-6}$cycloalkyl, $C_{1-6}$alkoxy, $C_{3-6}$alkenyloxy, $C_{3-6}$alkynyloxy, $C_{3-6}$cycloalkoxy, $C_{1-6}$alkyl-S(O)$_w$-(wherein w is 0, 1 or 2), $C_{1-6}$alkyl-N(R$^a$)—, $C_{1-6}$alkyl-N(R$^a$)-carbonyl-, $C_{1-6}$alkylcarbonyl-N(R$^a$)—, $C_{1-6}$alkyl-N(R$^a$)-carbonyl-N(R$^a$)—, $C_{1-6}$alkyl-N(R$^a$)—SO$_2$—, $C_{1-6}$alkyl-SO$_2$—N(R$^a$)—, $C_{1-6}$alkoxycarbonyl-N(R$^a$)—, $C_{1-6}$alkylcarbonyl-N(R$^a$)—$C_{1-6}$alkyl-, $C_{1-6}$alkyl-N(R$^a$)-carbonyl-$C_{1-6}$alkyl-, and $C_{1-6}$alkoxy$C_{1-6}$alkyl-; wherein $C_{1-6}$alkyl, $C_{2-6}$alkenyl, $C_{2-6}$alkynyl, $C_{3-6}$cycloalkyl, $C_{1-6}$alkoxy, $C_{3-6}$alkenyloxy, $C_{3-6}$alkynyloxy, $C_{3-6}$cycloalkoxy, $C_{1-6}$alkyl-S(O)$_w$—, $C_{1-6}$alkyl-N(R$^a$)—, $C_{1-6}$alkyl-N(R$^a$)-carbonyl-, $C_{1-6}$alkylcarbonyl-N(R$^a$)—, $C_{1-6}$alkyl-N(R$^a$)-carbonyl-N(R$^a$)—, $C_{1-6}$alkyl-N(R$^a$)—SO$_2$—, $C_{1-6}$alkyl-SO$_2$—N(R$^a$)—, $C_{1-6}$alkoxycarbonyl-N(R$^a$)—, $C_{1-6}$alkylcarbonyl-N(R$^a$)$C_{1-6}$alkyl-, $C_{1-6}$alkyl-N(R$^a$)-carbonyl-$C_{1-6}$alkyl-, and $C_{1-6}$alkoxy-$C_{1-6}$alkyl may optionally be substituted by a moiety selected from the group consisting of R$^P$, phenyl, phenoxy, heteroaryl, heteroaryloxy, heteroaryl-(NR$^a$)—, heterocyclyl, heterocyclyloxy and heterocyclyl-N(R$^a$)—; and wherein said heteroaryl and phenyl may optionally be substituted with one or more substituents selected from R$^f$; and wherein said heterocyclyl may optionally be substituted by one or more substituents selected from R$^g$; and wherein if said heterocyclyl contains a —NH moiety that nitrogen may optionally be substituted by one or more groups R$^h$;
$R^{D1}$ and $R^{D2}$ are each independently selected from the group consisting of: hydrogen, fluorine, hydroxyl, $C_{1-2}$alkyl and $C_{1-2}$alkoxy; wherein $C_{1-2}$alkyl and $C_{1-2}$alkoxy may be optionally substituted by one or more fluorine atoms or a group selected from cyano and hydroxyl;
$R^{D3}$ and $R^{D4}$ are each independently selected from the group consisting of: hydrogen, fluorine, hydroxyl, cyano, $C_{1-3}$alkyl and $C_{1-3}$alkoxy; wherein $C_{1-3}$alkyl and $C_{1-3}$alkoxy may optionally be substituted by one or more fluorine atoms or a group selected from cyano, hydroxyl and $N(R^aR^b)$;

$R^{D5}$ and $R^{D6}$ are each independently selected from the group consisting of: hydrogen, fluorine, hydroxyl, cyano, $C_{1-2}$alkyl and $C_{1-2}$alkoxy; wherein $C_{1-2}$alkyl and $C_{1-2}$alkoxy may optionally be substituted by one or more fluorine atoms or a group selected from cyano, hydroxyl and $N(R^aR^b)$;

$R^{N1}$ is selected from the group consisting of: hydrogen and $C_{1-2}$alkyl;

$R^{N2}$ is selected from the group consisting of: hydrogen, $C_{1-3}$alkyl and $C_{1-2}$alkylcarbonyl; wherein $C_{1-3}$alkyl and $C_{1-2}$alkylcarbonyl may optionally be substituted by one or more fluorine atoms or a group selected from cyano, hydroxyl and $N(R^aR^b)$;

$R^{N3}$ is selected from the group consisting of: hydrogen, $C_{1-3}$alkyl and $C_{1-2}$alkylcarbonyl; wherein $C_{1-3}$alkyl and $C_{1-2}$alkylcarbonyl may optionally be substituted by one or more fluorine atoms or a group selected from cyano, hydroxyl and $N(R^aR^b)$;

$R^a$ and $R^b$ are independently selected, for each occurrence, from the group consisting of: hydrogen and $C_{1-3}$alkyl; wherein $C_{1-3}$alkyl may optionally be substituted by one or more substituents selected from: fluorine, cyano, oxo and hydroxyl;

or $R^a$ and $R^b$, together with the nitrogen to which they are attached, may form a 4-6 membered heterocyclic ring which may have an additional heteroatom selected from the group consisting of O, S, and N; and wherein the 4-6 membered heterocyclic ring may optionally be substituted by one or more substituents selected from the group consisting of: fluorine, cyano, oxo and hydroxyl;

$R^f$ is independently selected, for each occurrence, from the group consisting of: $R^P$, hydrogen, $C_{1-6}$alkyl, $C_{3-6}$cycloalkyl, $C_{2-6}$alkenyl, $C_{2-6}$alkynyl, $C_{3-6}$cycloalkyl, $C_{1-6}$alkoxy, $C_{1-6}$alkyl-S(O)$_w$— (wherein w is 0, 1 or 2), $C_{1-6}$alkylcarbonyl-N($R^a$)—; and $C_{1-6}$alkoxycarbonyl-N($R^a$)—; wherein $C_{1-6}$alkyl, $C_{3-6}$cycloalkyl, $C_{2-6}$alkenyl, $C_{2-6}$alkynyl, $C_{3-6}$cycloalkyl, $C_{1-6}$alkoxy, $C_{1-6}$alkyl-S(O)$_w$—, $C_{1-6}$alkylcarbonyl-N($R^a$)—, and $C_{1-6}$alkoxycarbonyl-N($R^a$)— may be optionally substituted by one or more substituents selected from $R^P$;

$R^g$ is independently selected for each occurrence from the group consisting of: $R^P$, hydrogen, oxo, $C_{1-6}$alkyl, $C_{2-6}$alkenyl, $C_{2-6}$alkynyl, $C_{3-6}$cycloalkyl, $C_{1-6}$alkoxy, $C_{1-6}$alkyl-S(O)$_w$-(wherein w is 0, 1 or 2), $C_{1-6}$alkylcarbonyl-N($R^a$)—, and $C_{1-6}$alkoxycarbonyl-N($R^a$)—; wherein $C_{1-6}$alkyl, $C_{2-6}$alkenyl, $C_{2-6}$alkynyl, $C_{3-6}$cycloalkyl, $C_{1-6}$alkoxy, $C_{1-6}$alkyl-S(O)$_w$—, $C_{1-6}$alkylcarbonyl-N($R^a$)—, and $C_{1-6}$alkoxycarbonyl-N($R^a$)— may be optionally substituted by one or more substituents selected from $R^P$;

$R^h$ is independently selected for each occurrence from the group consisting of: hydrogen, $C_{1-6}$alkyl, $C_{3-6}$alkenyl, $C_{3-6}$alkynyl, $C_{3-6}$cycloalkyl, $C_{1-6}$alkyl-S(O)$_2$—, $C_{1-6}$alkoxycarbonyl-, $R^iR^jN$-carbonyl-, and $R^iR^jN$—SO$_2$—; wherein $C_{1-6}$alkyl, $C_{3-6}$alkenyl, $C_{3-6}$alkynyl, $C_{3-6}$cycloalkyl, $C_{1-6}$alkyl-S(O)$_2$—, and $C_{1-6}$alkylcarbonyl- may optionally be substituted by one or more substituents selected from $R^P$;

$R^i$ and $R^j$, are selected independently for each occurrence from the group consisting of: hydrogen, $C_{1-4}$alkyl and $C_{3-6}$cycloalkyl; wherein $C_{1-4}$alkyl and $C_{3-6}$cycloalkyl may optionally be substituted by one or more substituents selected from the group consisting of fluorine, hydroxyl, cyano, $R^aR^bN$—, $R^aR^bN$-carbonyl-, and $C_{1-3}$alkoxy;

or $R^i$ and $R^j$ taken together with the nitrogen to which they are attached form a 4-7 membered heterocyclic ring which may have an additional heteroatom selected from the group consisting of O, S, and N, optionally substituted on carbon by one or more substituents selected from the group consisting of: fluorine, hydroxyl, oxo, cyano, $C_{1-6}$alkyl, $C_{1-6}$alkoxy, $R^aR^bN$—, and $R^aR^bN$—SO$_2$—, $R^aR^bN$-carbonyl-; and wherein said $C_{1-6}$alkyl and $C_{1-6}$alkoxy may optionally be substituted by a group selected from fluorine, hydroxyl and cyano; and optionally substituted on nitrogen by one or more substituents selected from the group consisting of: $C_{1-6}$alkyl and $R^aR^bN$-carbonyl-; and wherein said $C_{1-6}$alkyl may be optionally substituted by a group selected from fluorine, hydroxyl, and cyano;

$R^P$ is independently selected, for each occurrence, from the group consisting of: halogen, hydroxyl, cyano, $C_{1-6}$alkoxy, $R^iR^jN$-, $R^iR^jN$-carbonyl-, $R^iR^jN$—SO$_2$—, and $R^iR^jN$-carbonyl-N($R^a$)—;

or a pharmaceutically acceptable salt, stereoisomer, or ester thereof.

2. The tricyclic compound of claim 1, wherein X is selected from the group consisting of $^+$—C($R^{D1}R^{D2}$)—C($R^{D5}R^{D6}$)—*, $^+$—O—C($R^{D5}R^{D6}$)—*, $^+$—N($R^{N1}$)—C($R^{D5}R^{D6}$)—*, and $^+$—O—C($R^{D3}R^{D4}$)—C($R^{D5}R^{D6}$)—*, wherein the $^+$ and * indicate the attachment points of X as indicated in Formula I.

3. The tricyclic compound of claim 1, wherein X is selected from the group consisting of $^+$—CH$_2$—CH$_2$-*, $^+$—O—CH$_2$-*, and $^+$—NH—CH$_2$-*;

wherein the $^+$ and * indicate the attachment points of X as indicated in Formula I.

4. The tricyclic compound of claim 1, wherein $R^{D1}$, $R^{D2}$, $R^{N1}$ and $R^{N2}$ that form part of X are independently selected from the group consisting of hydrogen and methyl.

5. The tricyclic compound of claim 1, wherein $R^{D1}$, $R^{D2}$, $R^{N1}$, and $R^{N2}$ that form part of X are hydrogen.

6. The tricyclic compound of claim 1, wherein $R^{D3}$, $R^{D4}$, $R^{D5}$ and $R^{D6}$ that form part of X are independently selected from the group consisting of hydrogen, fluorine, cyano, and $C_{1-2}$alkyl.

7. The tricyclic compound of claim 1, wherein $R^{D3}$, $R^{D4}$, $R^{D5}$ and $R^{D6}$ that form part of X are hydrogen.

8. The tricyclic compound of claim 1, wherein $R^{B1}$ and $R^{B2}$ are independently selected from the group consisting of H and methyl.

9. The tricyclic compound of claim 1, wherein $R^{B3}$ and $R^{B4}$ are independently selected from the group consisting of H and fluorine.

10. The tricyclic compound of claim 1, wherein the compound is represented by:

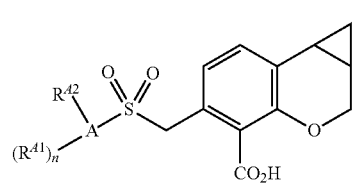

Ia

-continued

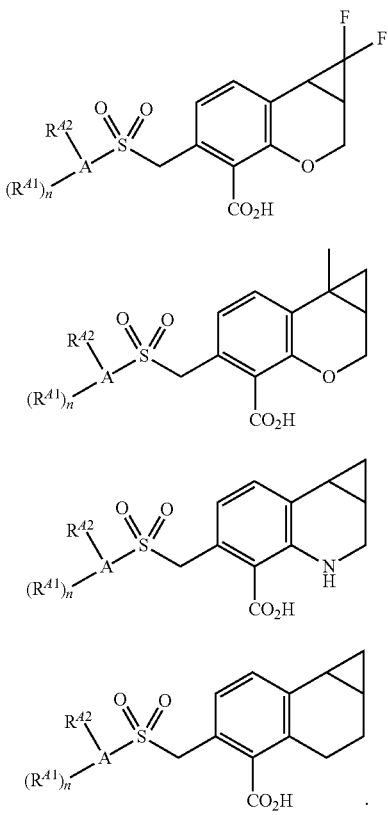

11. The tricyclic compound of claim 10, wherein A is phenyl.

12. A tricyclic compound represented by:

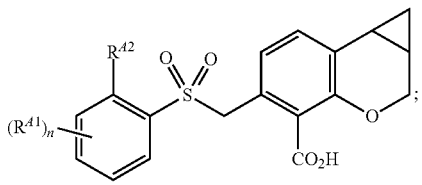

Formula II wherein:
$R^{A1}$ is selected from the group consisting of: hydrogen, halogen, $C_{1-2}$alkyl, and $C_{1-2}$alkoxy; wherein $C_{1-2}$alkyl may optionally be substituted by one or more fluorines;
$R^{A2}$ is selected from the group consisting of: hydrogen, $R^iR^jN$, heterocyclyl, $C_{1-6}$alkyl, $C_{3-6}$alkenyl, $C_{3-6}$cycloalkyl, and $C_{1-6}$alkoxy; wherein said heterocyclyl may optionally be substituted by one or more groups $R^g$, and wherein if said heterocyclyl contains a —NH moiety, that nitrogen may optionally be substituted by one or more groups $R^h$; and wherein said $C_{1-6}$alkyl, $C_{3-6}$alkenyl, $C_{3-6}$cycloalkyl and $C_{1-6}$alkoxy may optionally be substituted by one or more groups $R^P$;
n is 1 or 2;
$R^g$ is independently selected for each occurrence from the group consisting of: $R^P$, hydrogen, oxo, $C_{1-6}$alkyl, $C_{2-6}$alkenyl, $C_{2-6}$alkynyl, $C_{3-6}$cycloalkyl, $C_{1-6}$alkoxy, $C_{1-6}$alkyl-S(O)$_w$-(wherein w is 0, 1 or 2), $C_{1-6}$alkylcarbonyl-N($R^a$)—, and $C_{1-6}$alkoxycarbonyl-N($R^a$)—; wherein $C_{1-6}$alkyl, $C_{2-6}$ alkenyl, $C_{2-6}$alkynyl, $C_{3-6}$cycloalkyl, $C_{1-6}$alkoxy, $C_{1-6}$alkyl-S(O)$_w$—, $C_{1-6}$alkylcarbonyl-N($R^a$)—, and $C_{1-6}$alkoxycarbonyl-N($R^a$)— may be optionally substituted by one or more substituents selected from $R^P$;
$R^h$ is independently selected for each occurrence from the group consisting of: hydrogen, $C_{1-6}$alkyl, $C_{3-6}$alkenyl, $C_{3-6}$alkynyl, $C_{3-6}$cycloalkyl, $C_{1-6}$alkyl-S(O)$_2$—, $C_{1-6}$alkoxycarbonyl-, $R^iR^jN$-carbonyl-, and $R^iR^jN$—SO$_2$—; wherein $C_{1-6}$alkyl, $C_{3-6}$alkenyl, $C_{3-6}$alkynyl, $C_{3-6}$cycloalkyl, $C_{1-6}$alkyl-S(O)$_2$—, and $C_{1-6}$alkylcarbonyl- may optionally be substituted by one or more substituents selected from $R^P$;
$R^i$ and $R^j$ are selected independently for each occurrence from the group consisting of: hydrogen, $C_{1-4}$alkyl and $C_{3-6}$cycloalkyl; wherein $C_{1-4}$alkyl and $C_{3-6}$cycloalkyl may be optionally substituted by one or more substituents selected from the group consisting of fluorine, hydroxyl, cyano, $R^aR^bN$—, $R^aR^bN$-carbonyl-, and $C_{1-3}$ alkoxy;
or $R^i$ and $R^j$ taken together with the nitrogen to which they are attached form a 4-7 membered heterocyclic ring which may have an additional heteroatom selected from the group consisting of O, S, and N, optionally substituted on carbon by one or more substituents selected from the group consisting of: fluorine, hydroxyl, oxo, cyano, $C_{1-6}$alkyl, $C_{1-6}$alkoxy, $R^aR^bN$—, $R^aR^bN$—SO$_2$—, and $R^aR^bN$-carbonyl-; and wherein said $C_{1-6}$alkyl and $C_{1-6}$alkoxy may optionally be substituted by a group selected from fluorine, hydroxyl and cyano; and optionally substituted on nitrogen by one or more substituents selected from the group consisting of: $C_{1-6}$alkyl and $R^aR^bN$-carbonyl-; and wherein said $C_{1-6}$alkyl may be optionally substituted by a group selected from fluorine, hydroxyl, and cyano;
$R^P$ is independently selected, for each occurrence, from the group consisting of: halogen, hydroxyl, cyano, $C_{1-6}$alkoxy, $R^iR^jN$-carbonyl-, $R^iR^jN$—SO$_2$—, and $R^iR^jN$-carbonyl-N($R^a$)—;
$R^a$ and $R^b$ are independently selected, for each occurrence, from the group consisting of: hydrogen and $C_{1-3}$alkyl; wherein $C_{1-3}$alkyl may optionally be substituted by one or more substituents selected from the group consisting of: fluorine, cyano, oxo and hydroxyl;
or $R^a$ and $R^b$, together with the nitrogen to which they are attached, may form a 4-6 membered heterocyclic ring which may have an additional heteroatom selected from the group consisting of O, S, and N; and wherein the 4-6 membered heterocyclic ring may optionally be substituted by one or more substituents selected from the group consisting of: fluorine, cyano, oxo and hydroxyl;
or a pharmaceutically acceptable salt, stereoisomer thereof.

13. The tricyclic compound of claim 12, wherein $R^{A1}$ is selected from the group consisting of hydrogen and fluorine.

14. A compound selected from the group consisting of: cis-(1aRS,7bSR)-5-[2-((Z)-3-diethylaminoprop-1-enyl)-4-fluoro-benzenesulfonylmethyl]-1,1a,2,7b-tetrahydrocyclopropa[c]chromene-4-carboxylic acid; cis-(1aR,7bS)-5-[2-((Z)-3-diethylaminoprop-1-enyl)-4-fluoro-benzenesulfonylmethyl]-1,1a,2,7b-tetrahydrocyclopropa[c]chromene-4-carboxylic acid; cis-(1aS,7bR)-5-[2-((Z)-3-diethylaminoprop-1-enyl)-4-fluoro-benzenesulfonylmethyl]-1,1a,2,7b-tetrahydrocyclopropa[c]

chromene-4-carboxylic acid; and a pharmaceutically acceptable salt, stereoisomer, or ester thereof.

15. A pharmaceutically acceptable composition comprising a compound of claim 1 and a pharmaceutically acceptable excipient.

16. A method of inducing weight loss in a patient in need thereof, comprising administering to said patient an effective amount of a compound of claim 1.

17. The method of claim 16, wherein the patient is a human.

18. The method of claim 16, wherein the patient is a cat or dog.

19. The method of claim 16, wherein the patient has a body mass index greater than or equal to about 30 kg/m$^2$ before the administration.

20. The method of claim 16, wherein the compound is administered orally.

21. The composition of claim 15, wherein the composition is formulated as a unit dose.

22. The composition of claim 15, wherein the composition is formulated for oral administration.

23. The composition of claim 15, wherein the composition is formulated for intravenous or subcutaneous administration.

* * * * *